US010959789B2

United States Patent
Yi et al.

(10) Patent No.: US 10,959,789 B2
(45) Date of Patent: Mar. 30, 2021

(54) VASCULAR INTERVENTION ROBOT AND VASCULAR INTERVENTION SYSTEM

(71) Applicants: INDUSTRY-ACADEMIC COOPERATION FOUNDATION, YONSEI UNIVERSITY, Seoul (KR); INDUSTRY-UNIVERSITY COOPERATION FOUNDATION HANYANG UNIVERSITY ERICA CAMPUS, Seoul (KR)

(72) Inventors: Byungju Yi, Bucheon-si (KR); Hyojeong Cha, Ansan-si (KR); Kwanyoung Jung, Ansan-si (KR); Jongyoon Won, Seoul (KR)

(73) Assignees: INDUSTRY-UNIVERSITY COOPERATION FOUNDATION HANYANG UNIVERSITY ERICA CAMPUS, Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 314 days.

(21) Appl. No.: 15/843,221

(22) PCT Filed: Jun. 2, 2016

(86) PCT No.: PCT/KR2016/005857
§ 371 (c)(1),
(2) Date: Dec. 15, 2017

(87) PCT Pub. No.: WO2016/204437
PCT Pub. Date: Dec. 22, 2016

(65) Prior Publication Data
US 2018/0168751 A1 Jun. 21, 2018

(30) Foreign Application Priority Data

Jun. 16, 2015 (KR) .................. 10-2015-0085253
Jun. 23, 2015 (KR) .................. 10-2015-0089044

(51) Int. Cl.
*A61B 34/30* (2016.01)
*A61B 34/37* (2016.01)
(Continued)

(52) U.S. Cl.
CPC .............. *A61B 34/30* (2016.02); *A61B 34/37* (2016.02); *A61B 90/00* (2016.02);
(Continued)

(58) Field of Classification Search
CPC ... A61B 2034/301; A61B 34/30; A61B 34/37; A61B 34/70; A61B 90/60; A61M 25/0113; A61M 25/09041; A61M 25/0116
See application file for complete search history.

(56) References Cited

U.S. PATENT DOCUMENTS 7,887,549 B2 * 2/2011 Wenderow ......... A61M 25/0113
606/108
7,974,674 B2 7/2011 Hauck et al.
(Continued)

FOREIGN PATENT DOCUMENTS

JP 5478511 B2 4/2014

OTHER PUBLICATIONS

Cha et al., "A robotic system for Vascular Intervention to reduce radiation exposure," The 10th Korea Robotics Society Annual Conference, May 2015, pp. 453-455.
(Continued)

*Primary Examiner* — Sarah W Aleman
(74) *Attorney, Agent, or Firm* — Sughrue Mion, PLLC

(57) ABSTRACT

A vascular intervention robot includes a catheter rotation unit for rotating a catheter on an axis parallel to a longitu-
(Continued)

dinal direction of the catheter, a guide wire rotation and supply unit that is provided at one side of the catheter rotation unit and that is provided for transferring a guide wire in a longitudinal direction of the guide wire and for rotating the guide wire on an axis parallel to the longitudinal direction of the guide wire in a state in which the guide wire is inserted in the catheter, a transfer unit for transferring the catheter rotation unit and the guide wire rotation and supply unit in the longitudinal direction of the catheter, and an expanding and contracting unit that is provided at another side of the catheter rotation unit and that is expandable and contractible along the longitudinal direction of the catheter while supporting the catheter when the transfer unit transfers the catheter rotation unit and the guide wire rotation and supply unit in the longitudinal direction of the catheter.

9 Claims, 40 Drawing Sheets

(51) Int. Cl.
*A61M 25/01* (2006.01)
*A61M 25/09* (2006.01)
*A61B 90/00* (2016.01)
*A61B 90/57* (2016.01)

(52) U.S. Cl.
CPC .... *A61M 25/0116* (2013.01); *A61B 2034/301* (2016.02); *A61B 2034/303* (2016.02); *A61B 2090/571* (2016.02); *A61M 25/0113* (2013.01); *A61M 25/09041* (2013.01); *A61M 2210/12* (2013.01)

(56) References Cited

U.S. PATENT DOCUMENTS

| | | | |
|---|---|---|---|
| 8,187,229 B2 | 5/2012 | Weitzner et al. | |
| 9,427,562 B2* | 8/2016 | Blacker | A61M 39/10 |
| 2008/0009791 A1* | 1/2008 | Cohen | A61B 34/30 |
| | | | 604/95.01 |
| 2008/0033284 A1* | 2/2008 | Hauck | A61B 90/10 |
| | | | 600/424 |
| 2011/0028894 A1 | 2/2011 | Foley et al. | |

OTHER PUBLICATIONS

International Search Report for PCT/KR2016/005857, dated Sep. 12, 2016.

* cited by examiner

【Fig. 1】
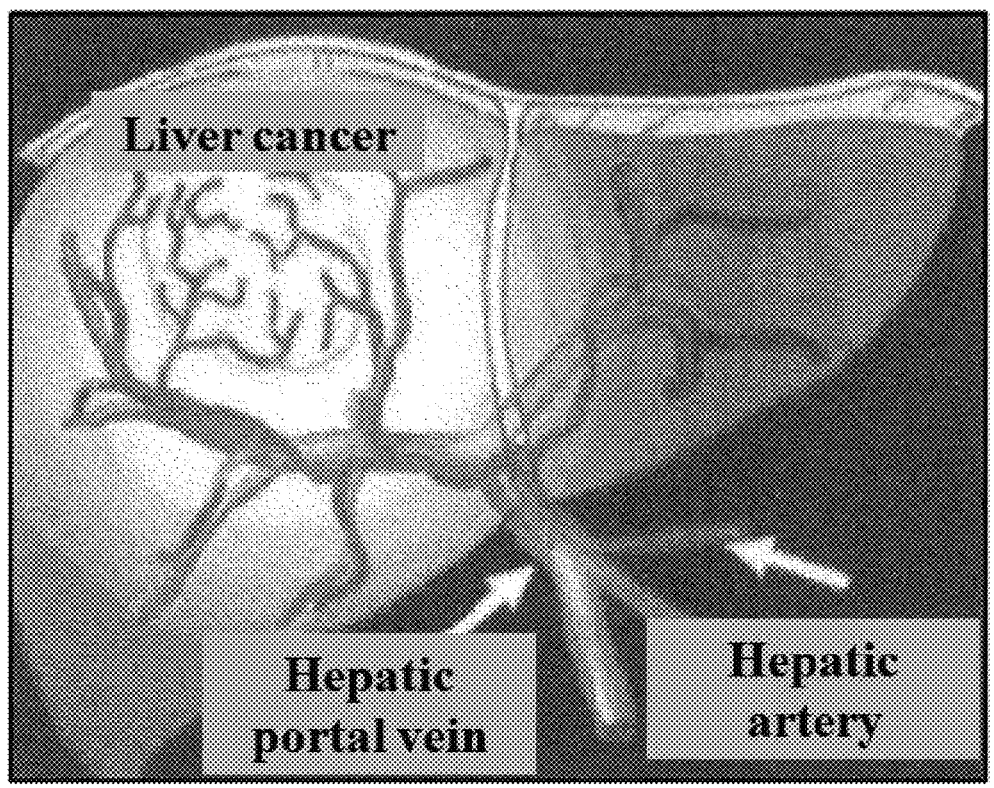
【Fig. 2】
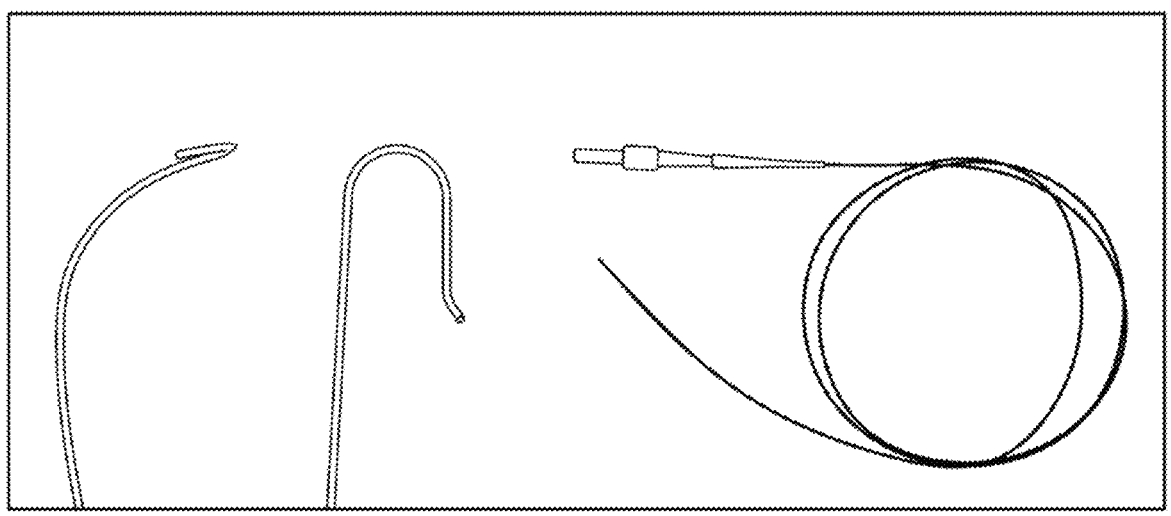

[Fig. 3]
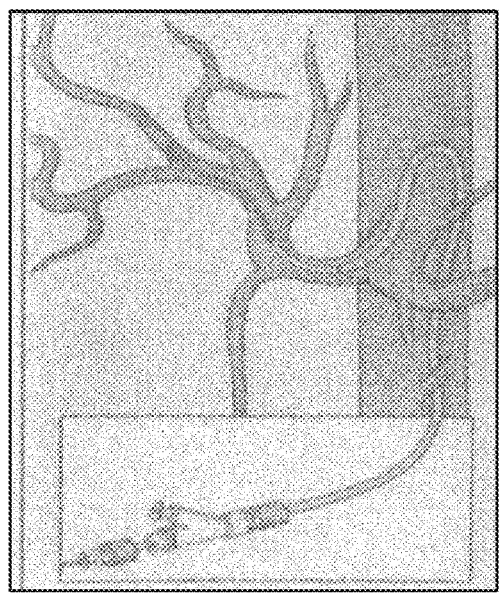
[Fig. 4]

[Fig. 5]
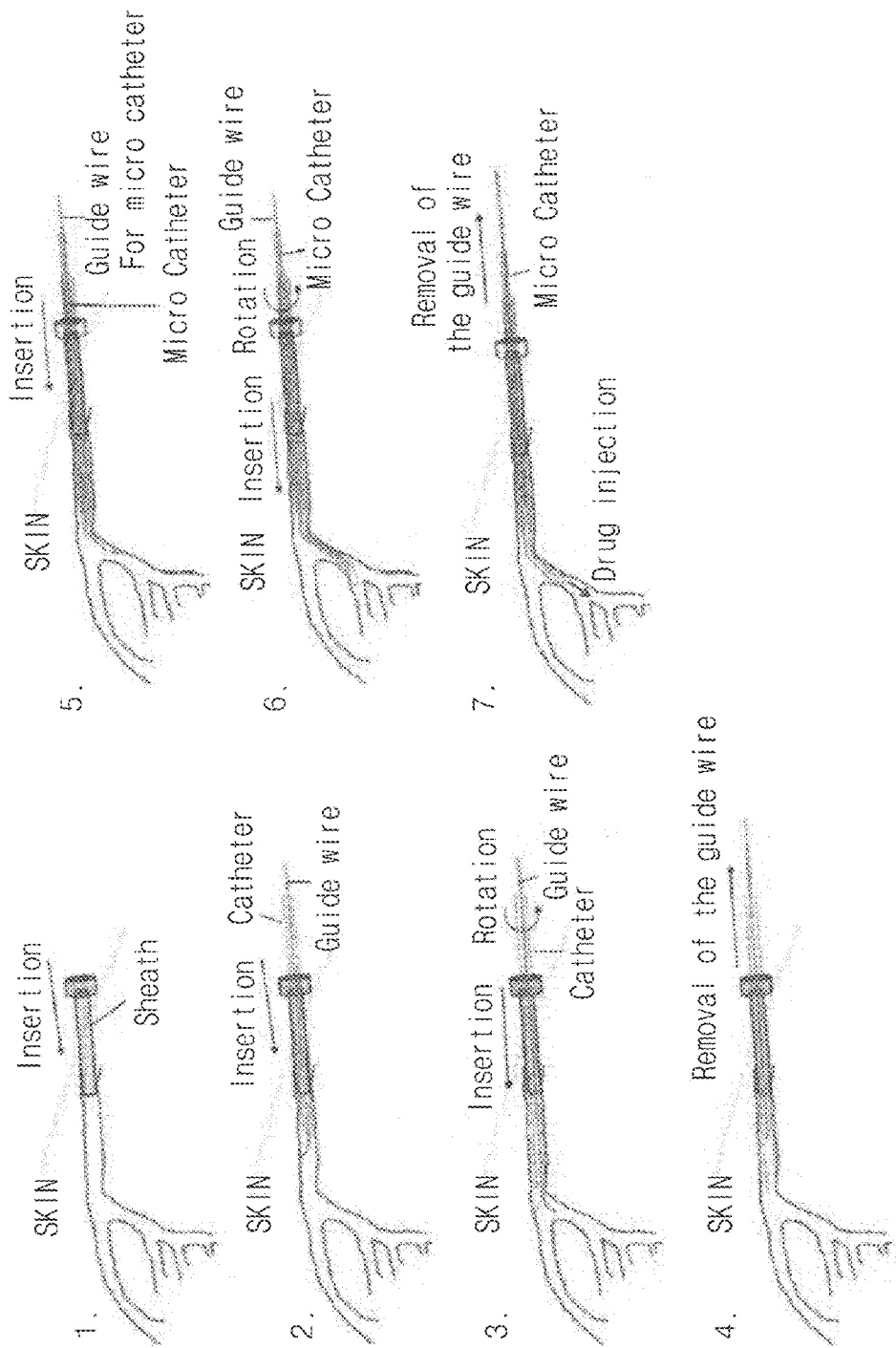

[Fig. 6]
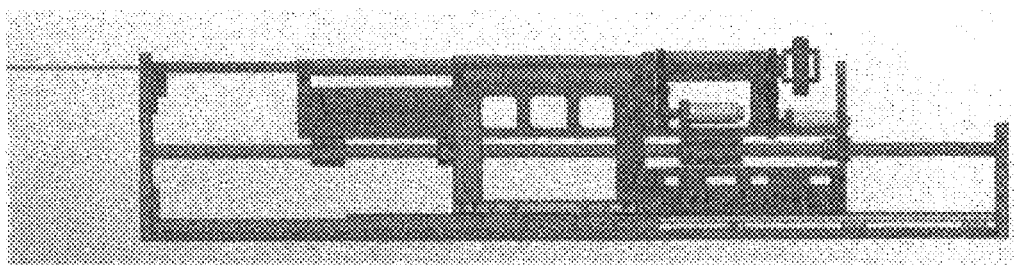
[Fig. 7]
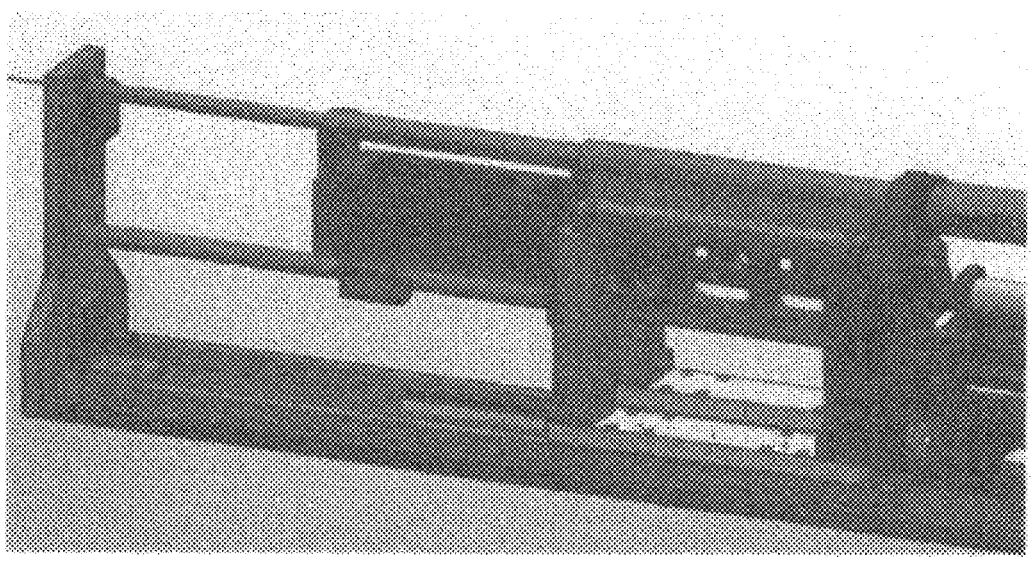

[Fig. 8]
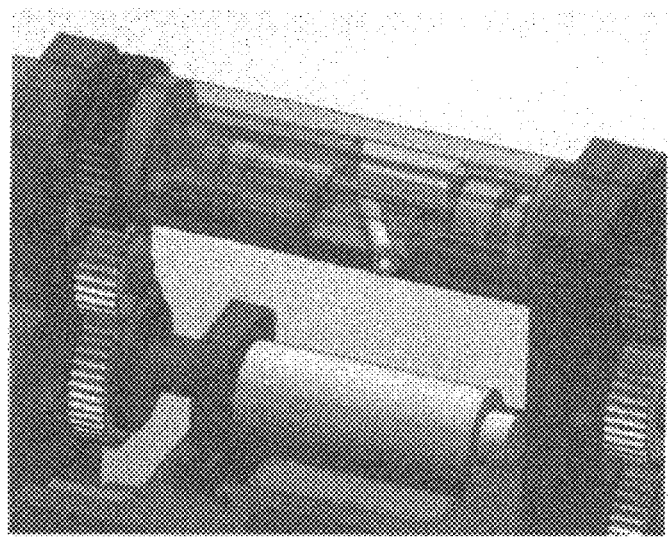
[Fig. 9]
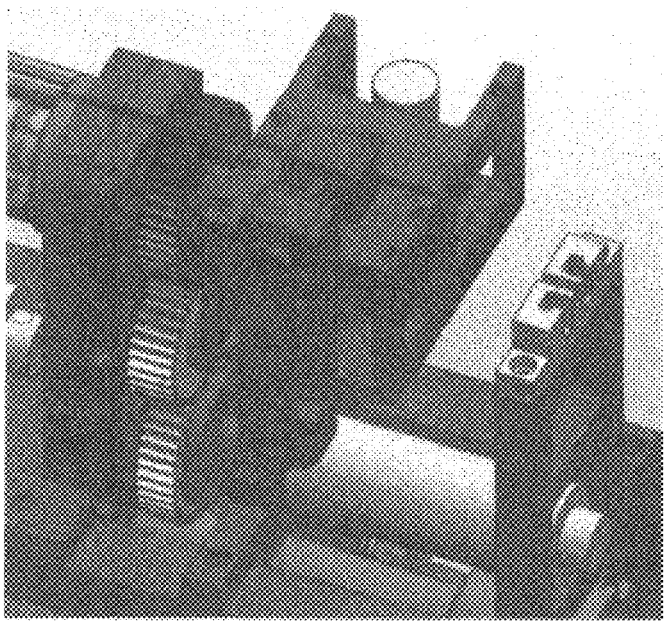

[Fig. 10]
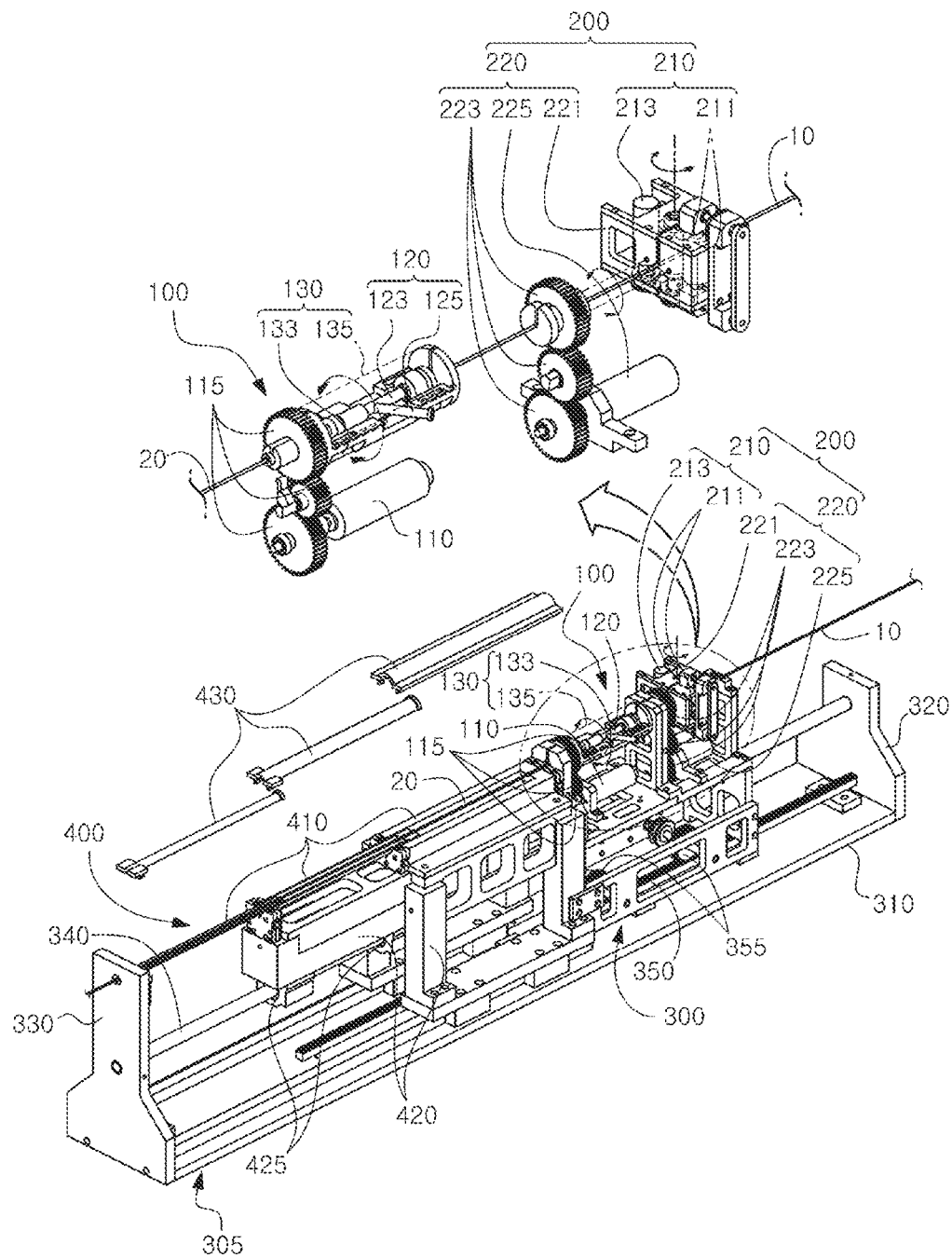

[Fig. 11]
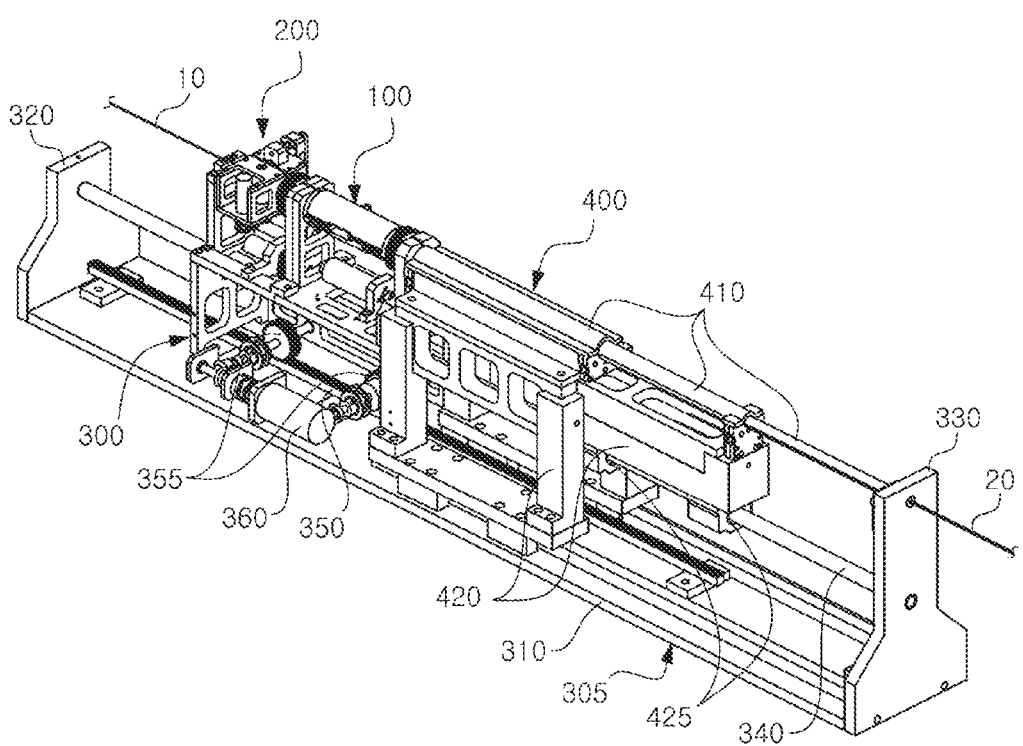

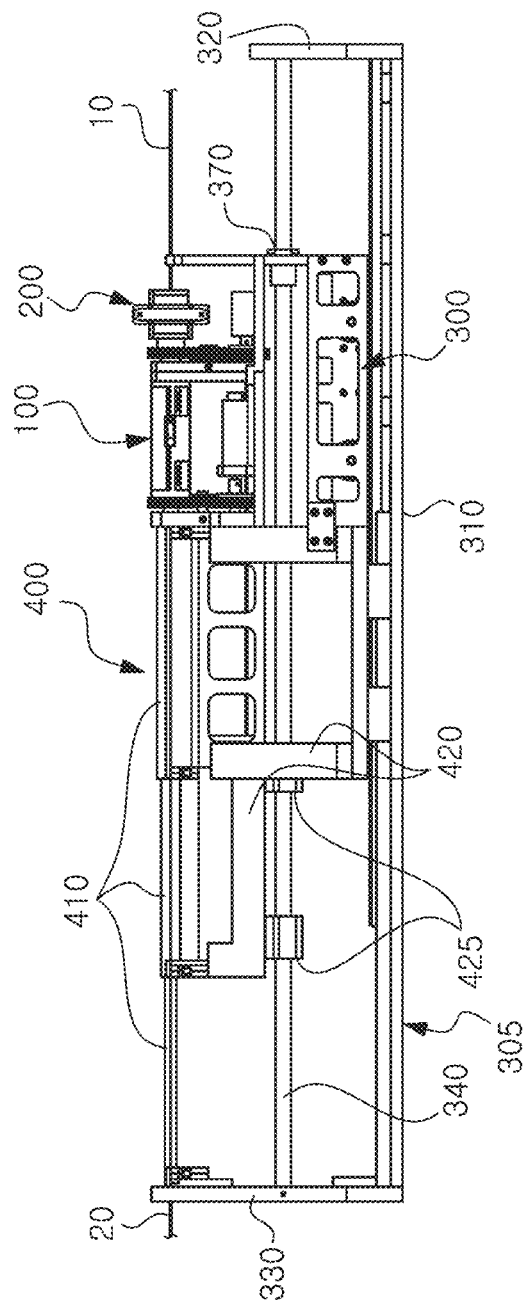
[Fig. 12]

[Fig. 13]
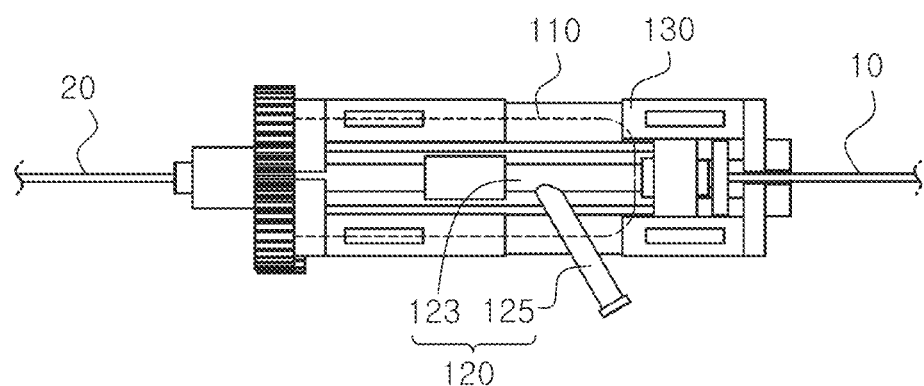
[Fig. 14]
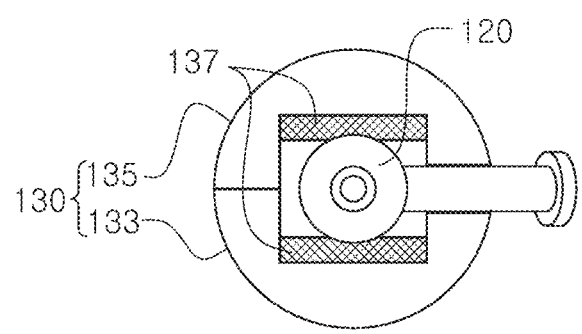

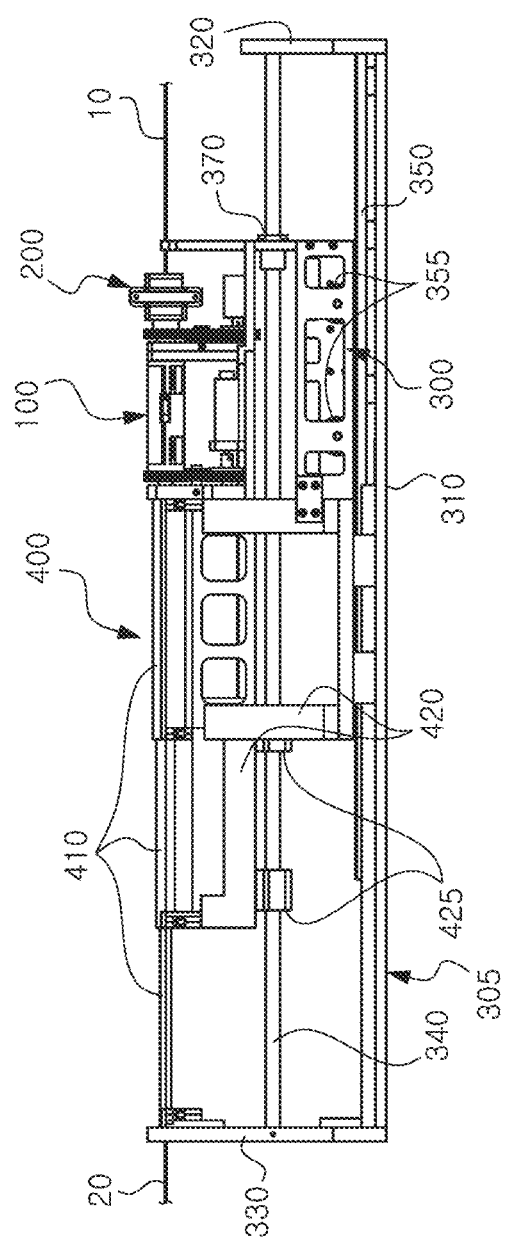
[Fig. 15a]

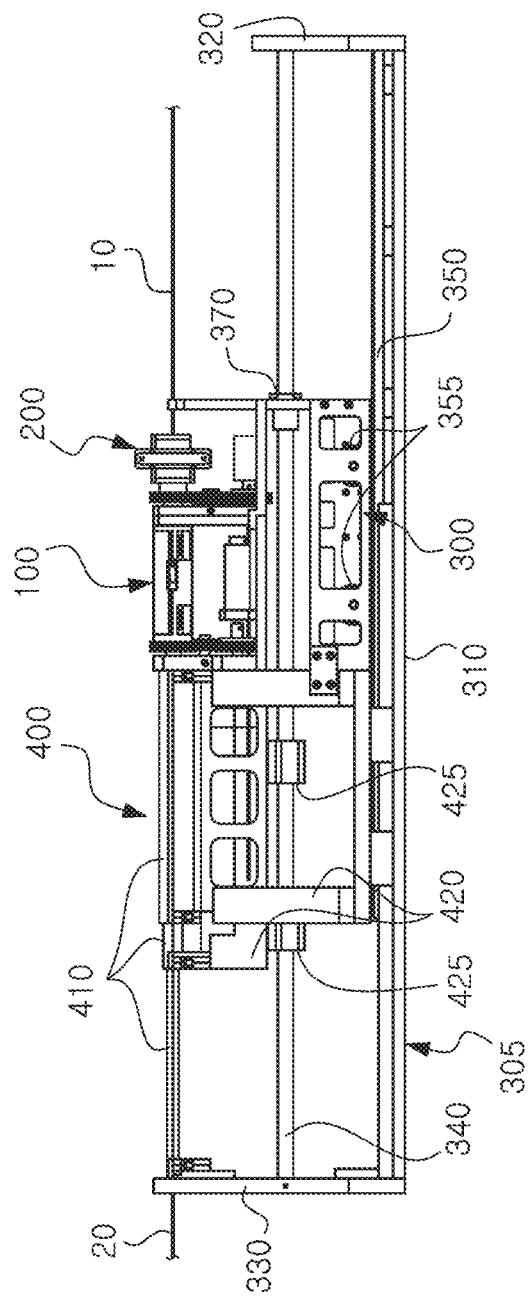
[Fig. 15b]

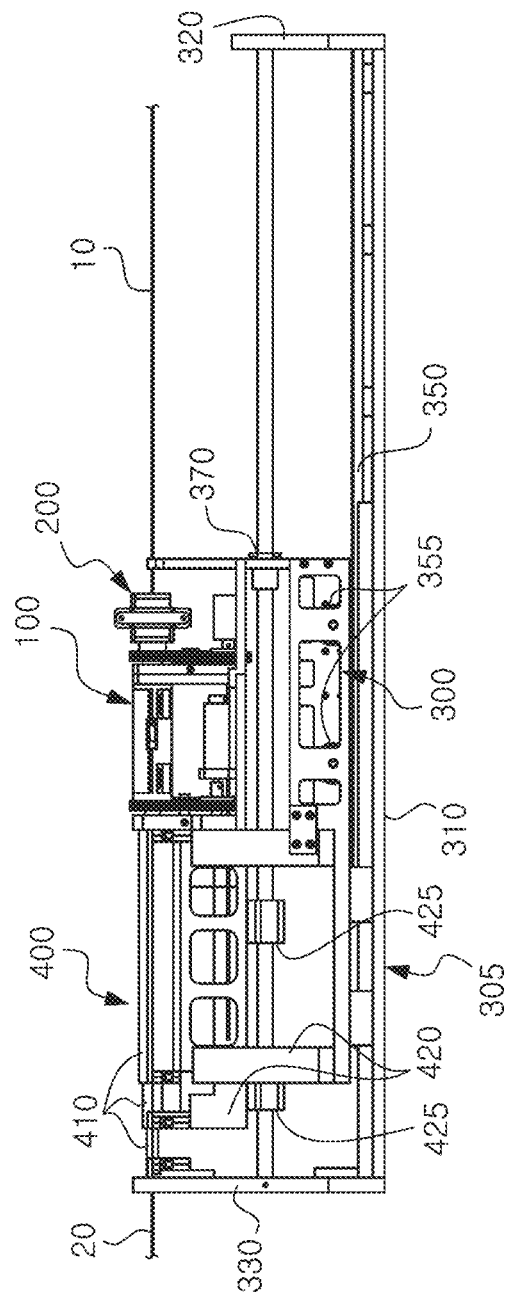
[Fig. 15c]

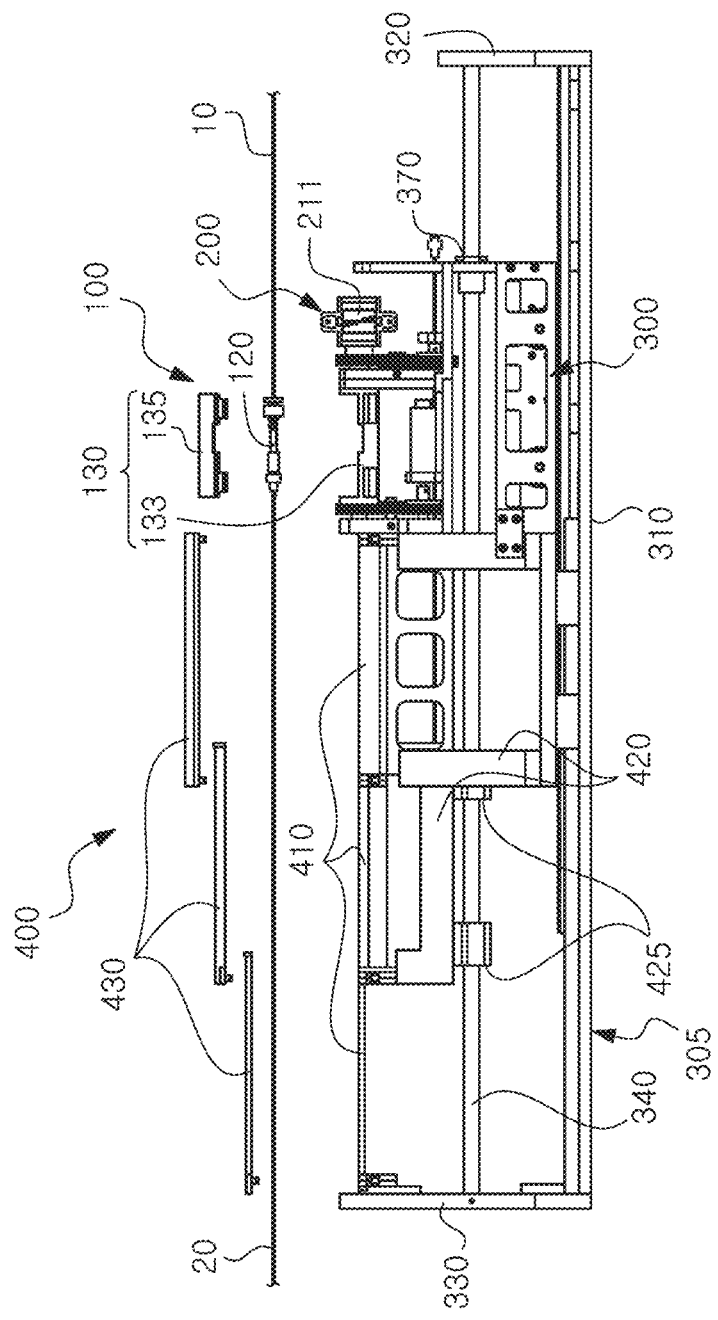
[Fig. 16a]

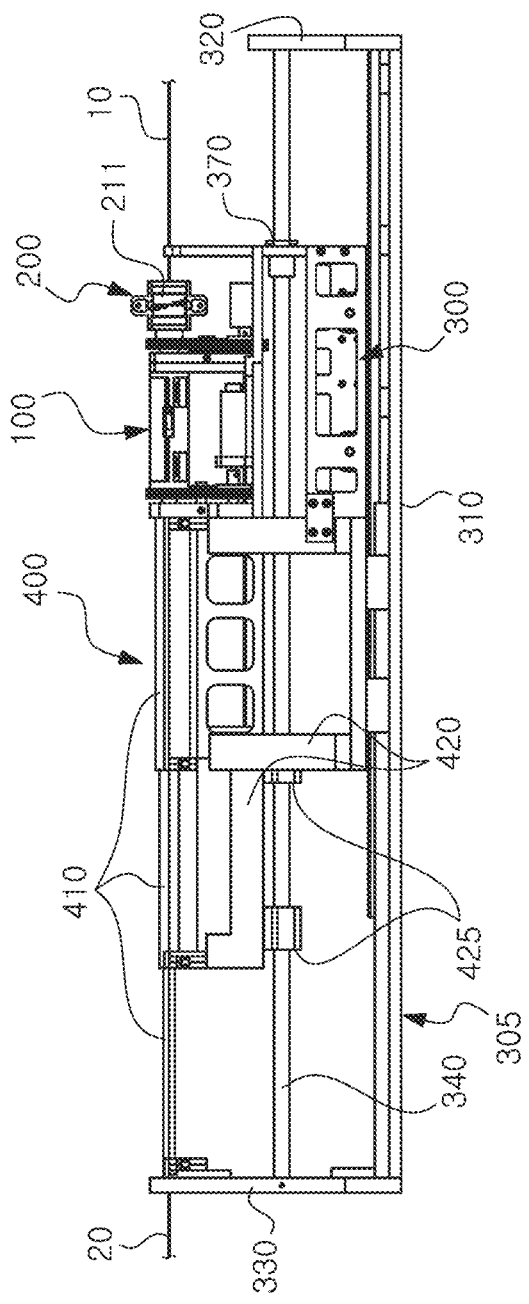
[Fig. 16b]

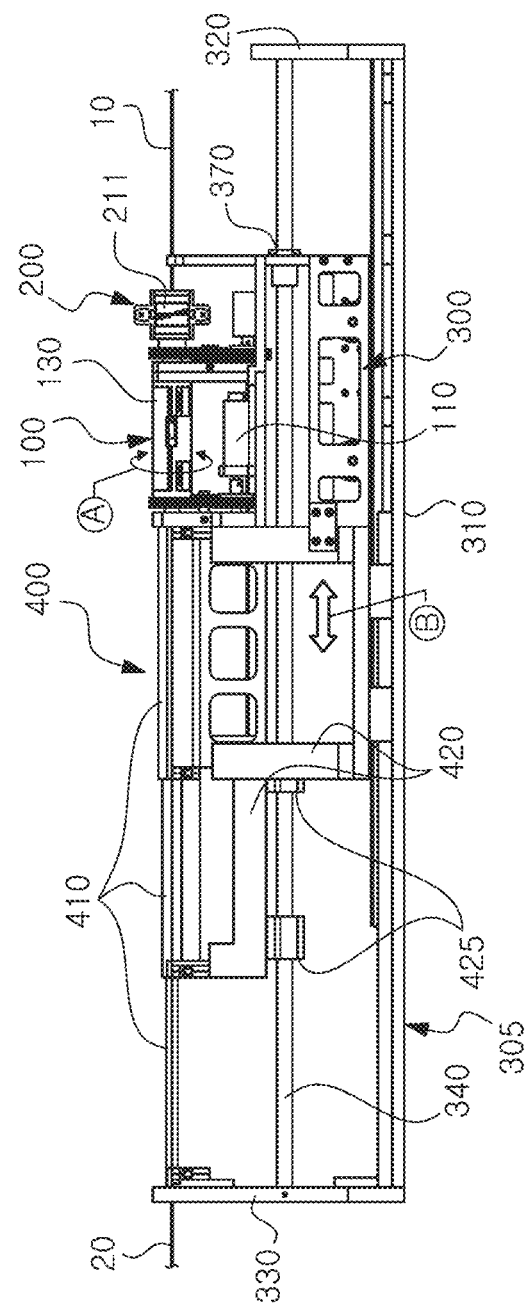
[Fig. 17]

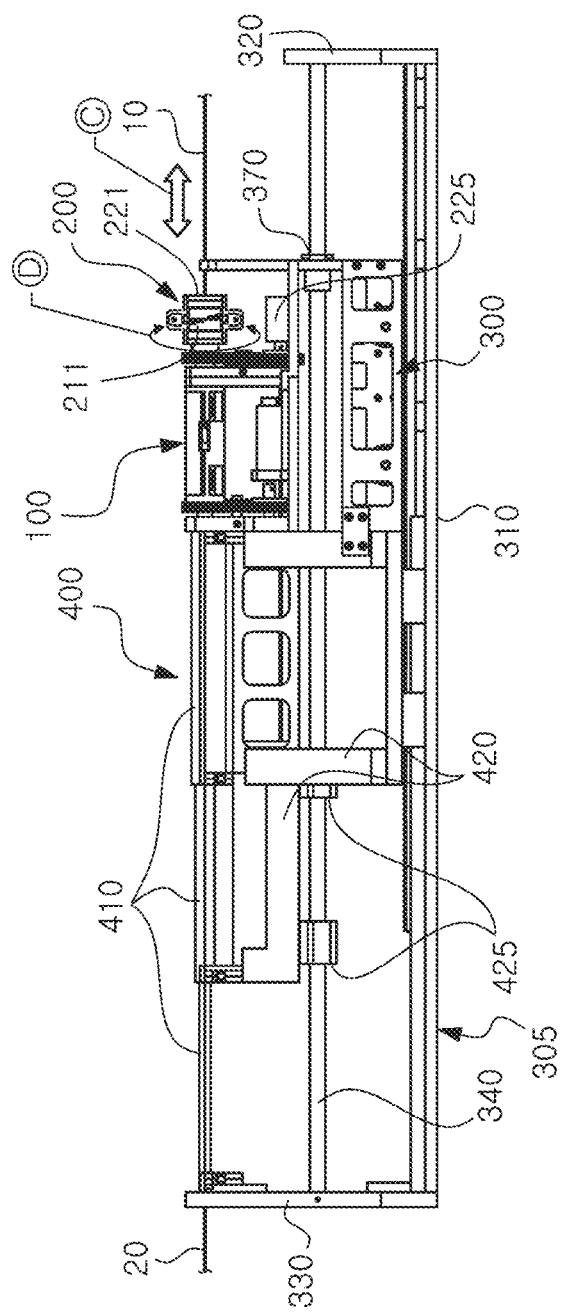
[Fig. 18]

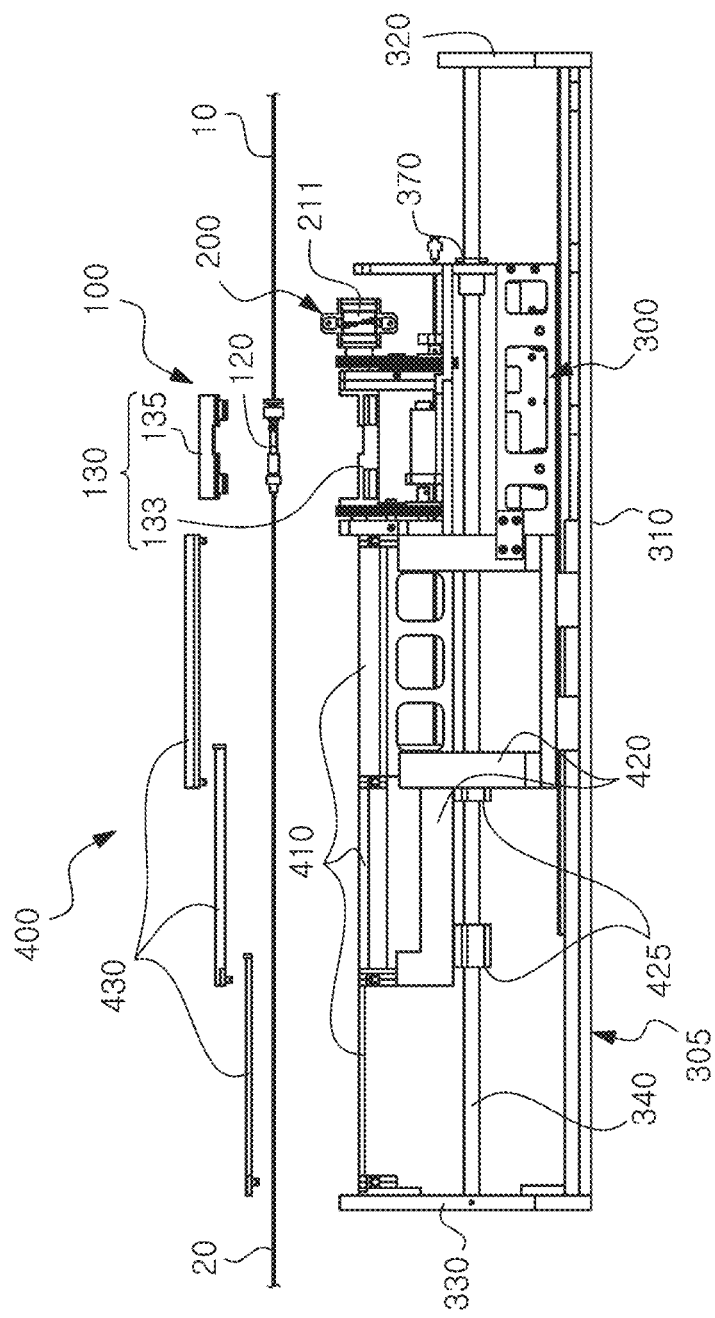
[Fig. 19]

[Fig.20]
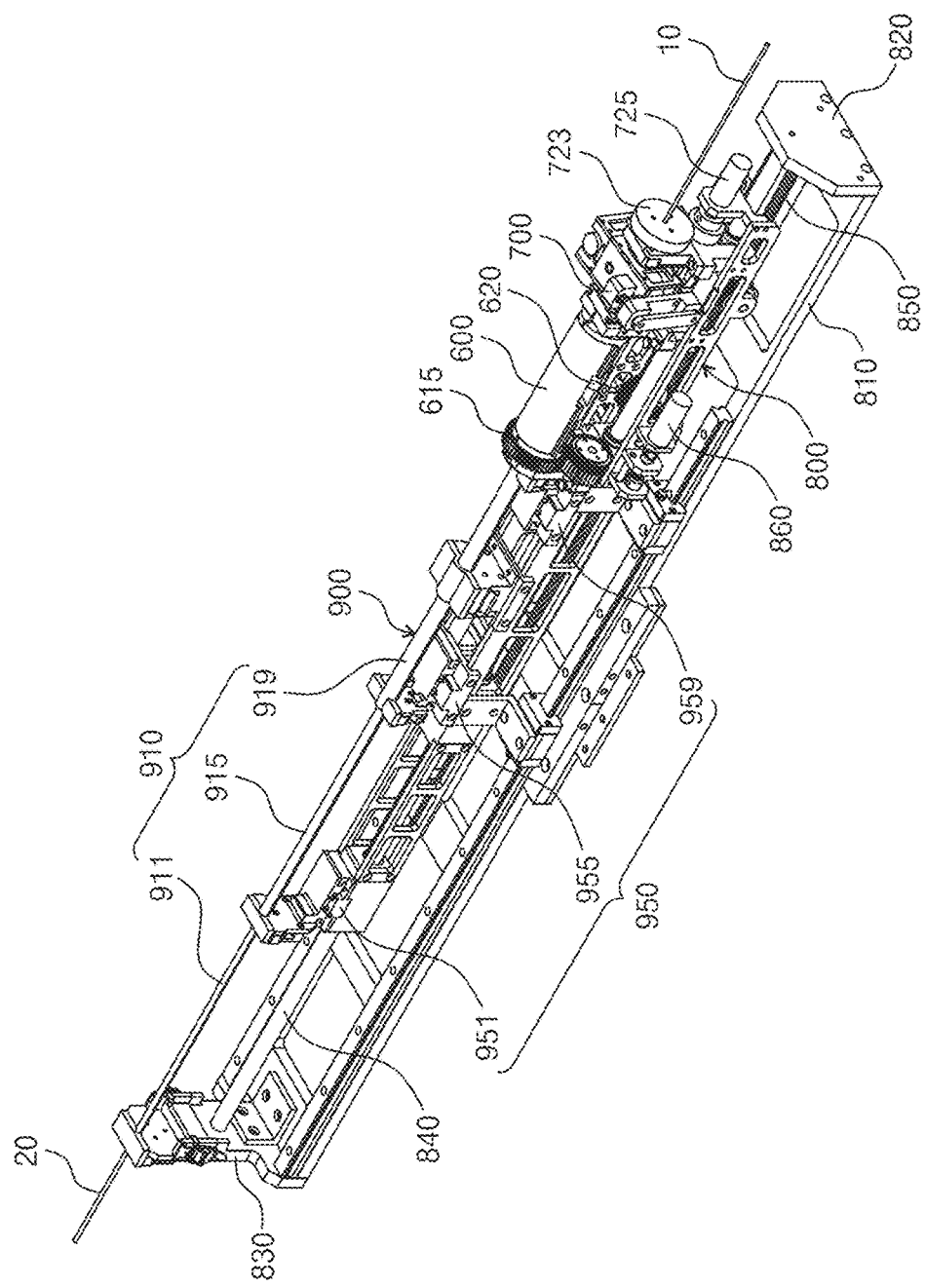

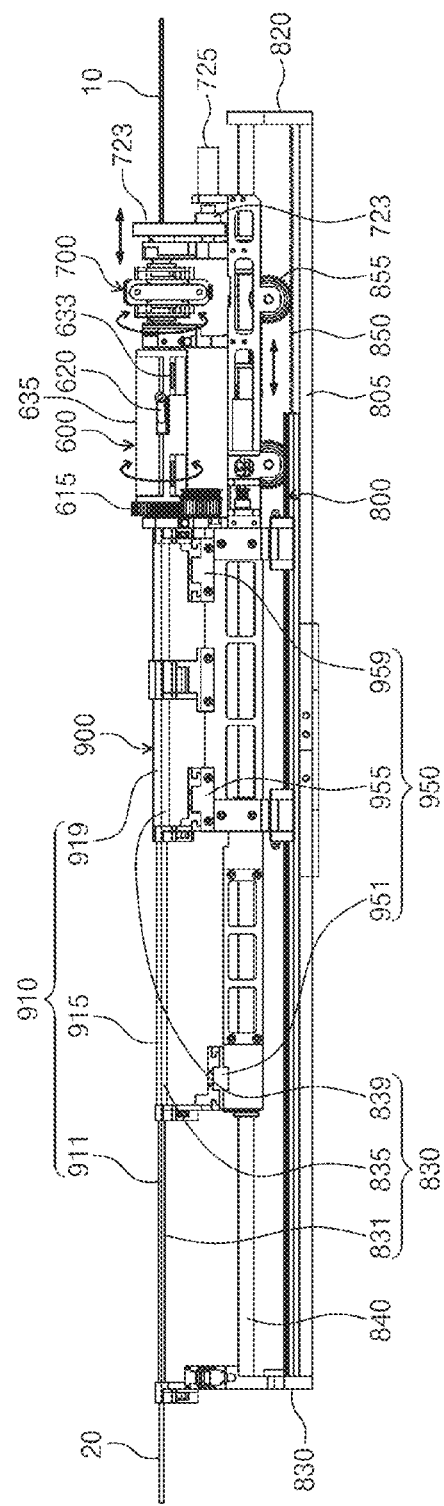
[Fig. 21]

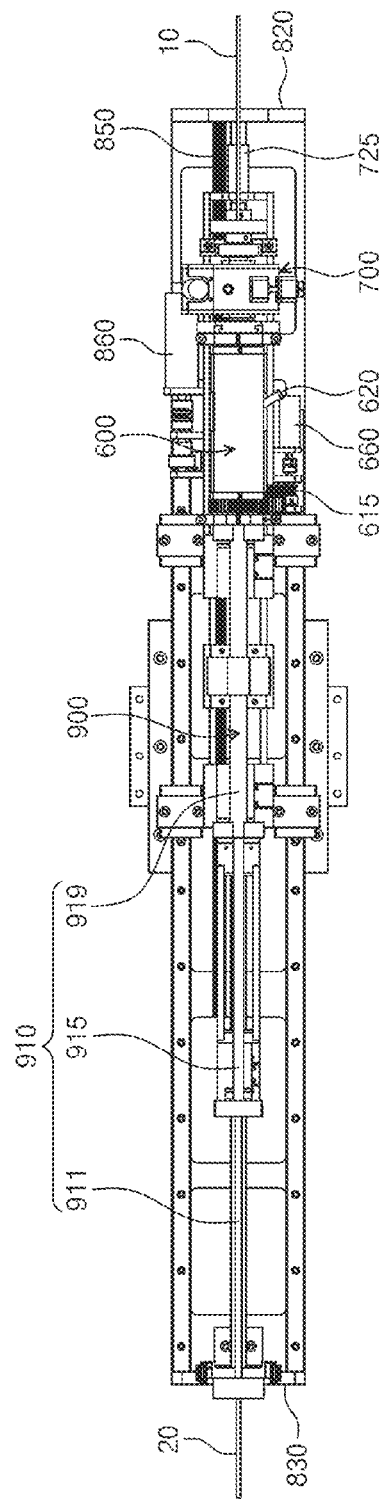
[Fig. 22]

[Fig. 23]
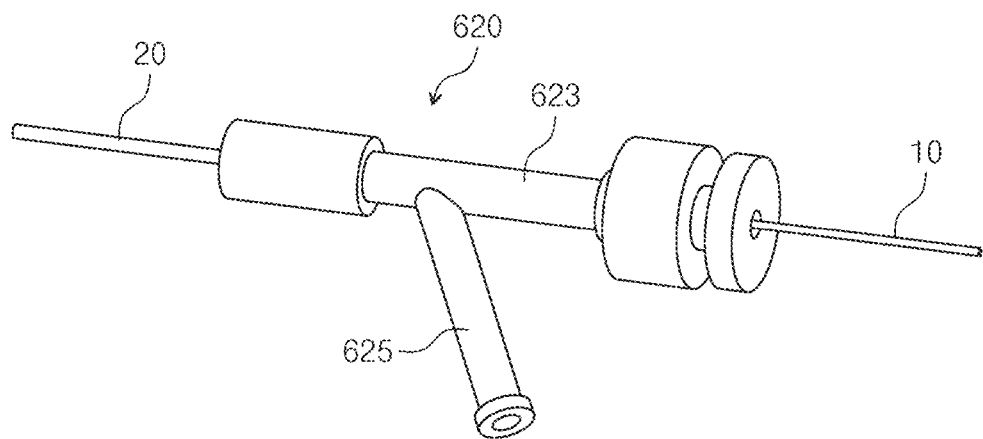
[Fig. 24a]
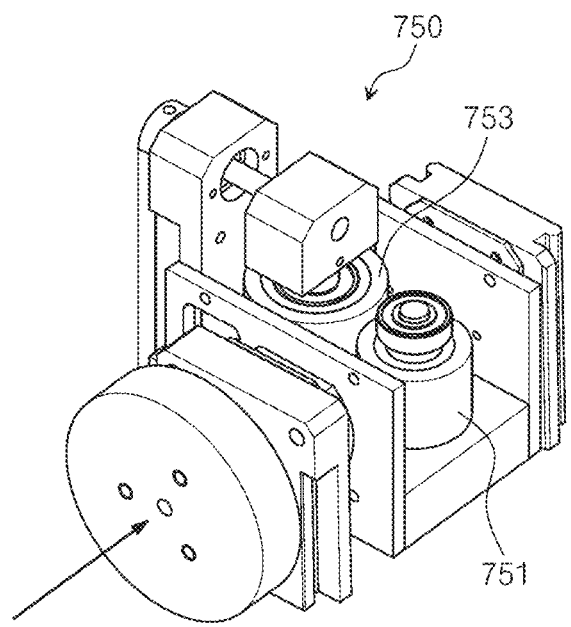

[Fig. 24b]
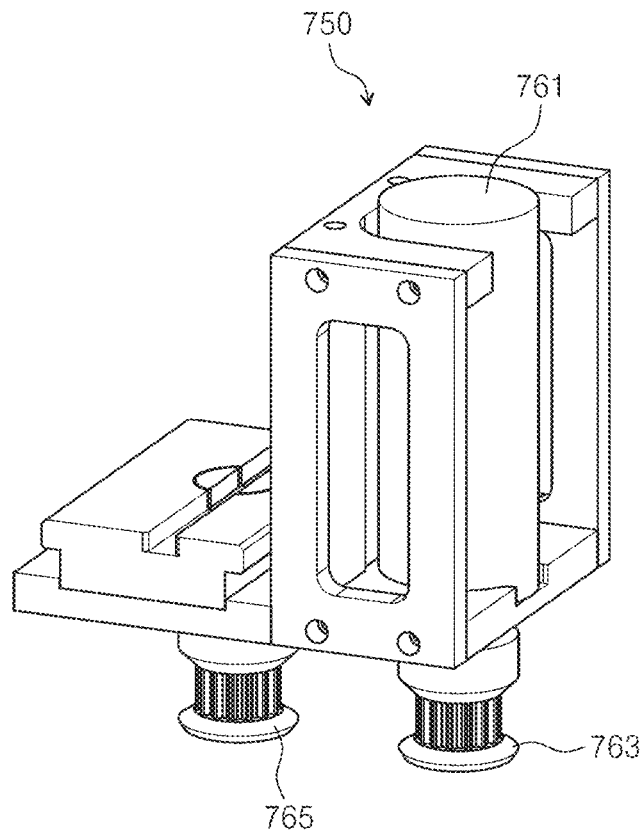
[Fig. 25a]
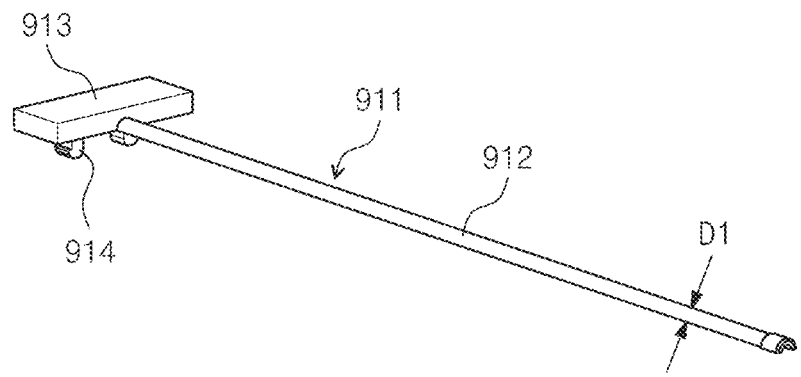

[Fig. 25b]
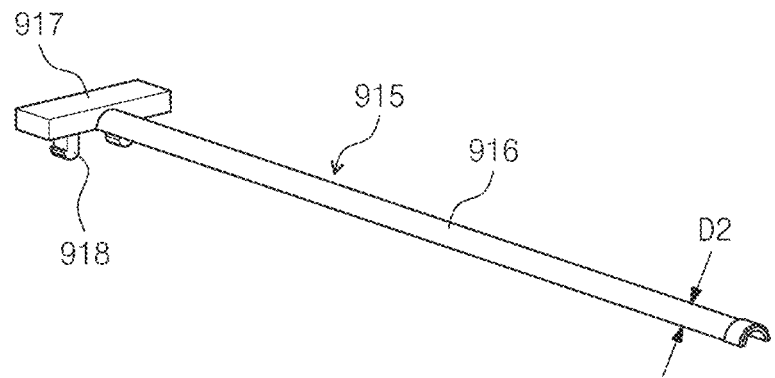
[Fig. 25c]
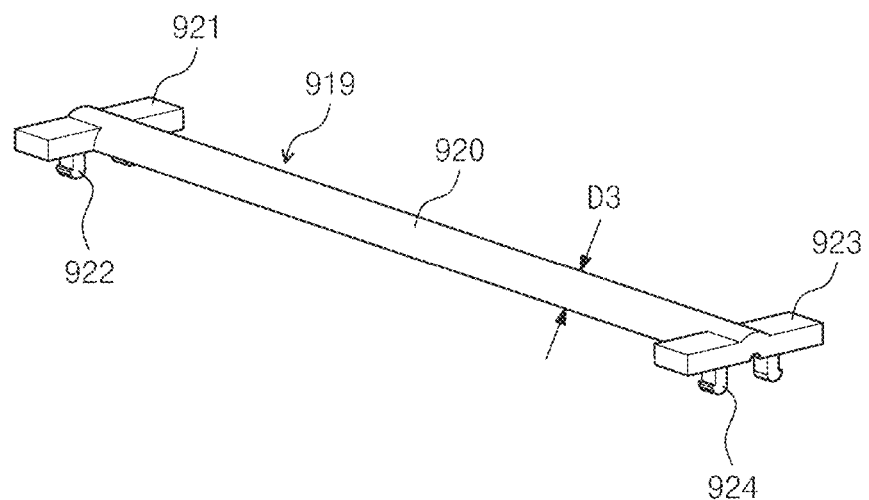
[Fig. 26a]
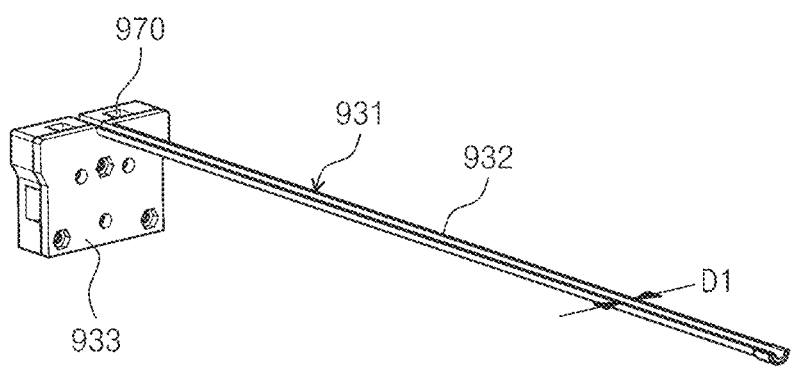

[Fig. 26b]
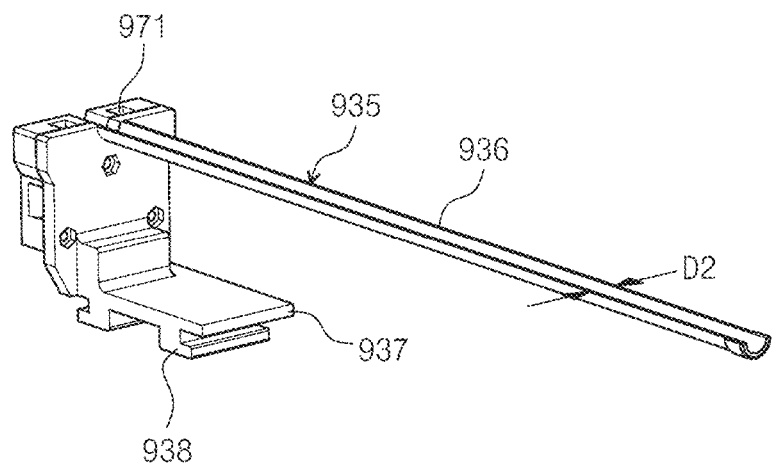
[Fig. 26c]
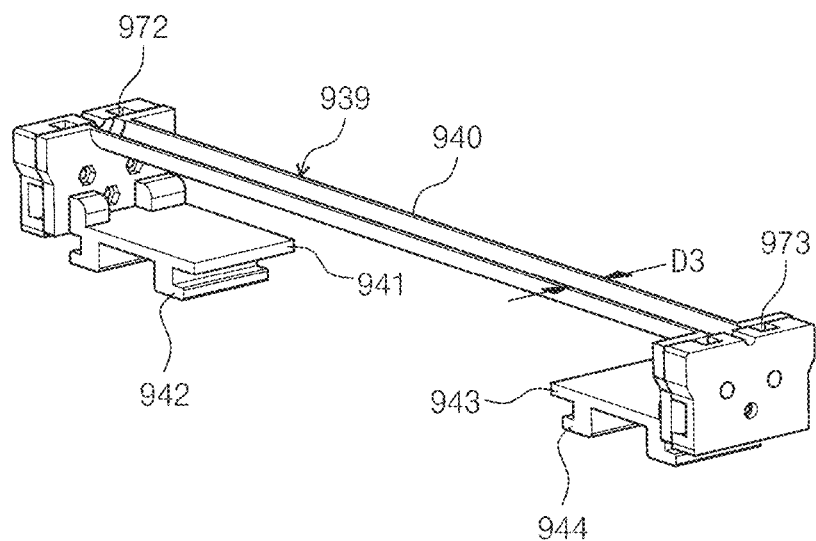

[Fig. 27]
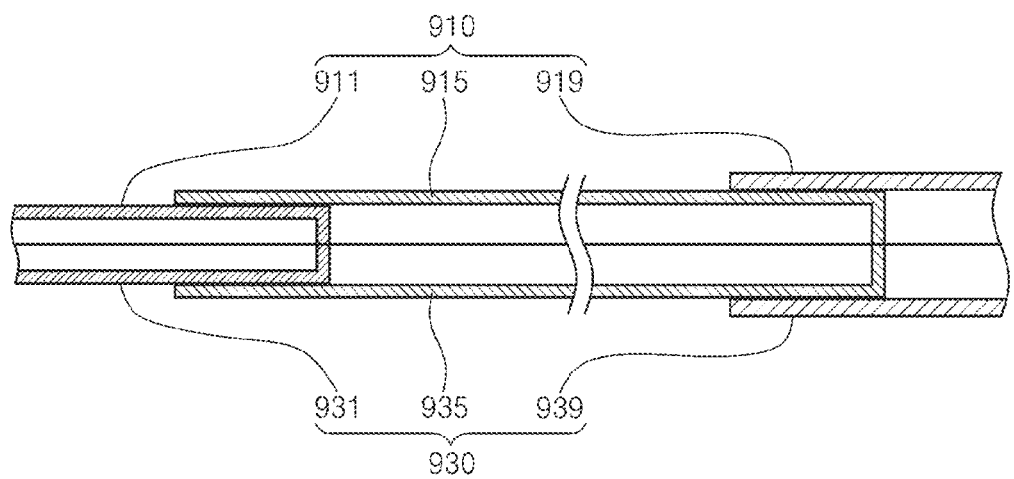
[Fig. 28]
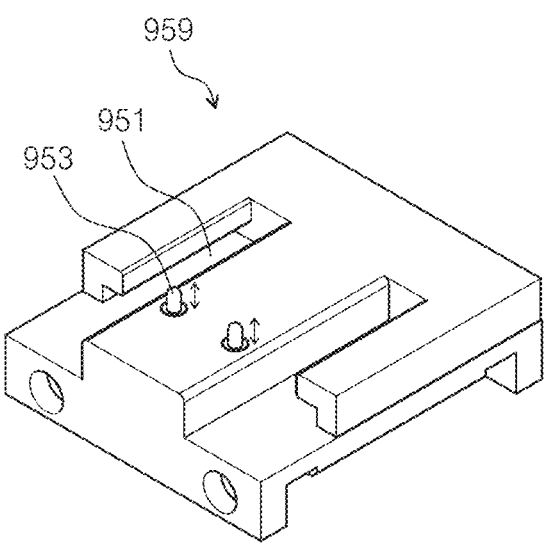

[Fig. 29]
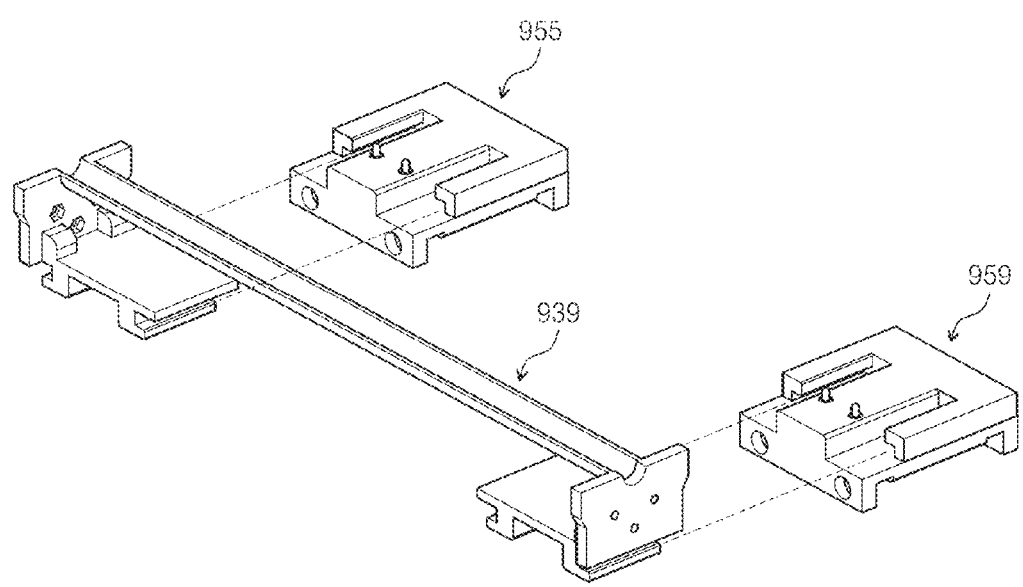

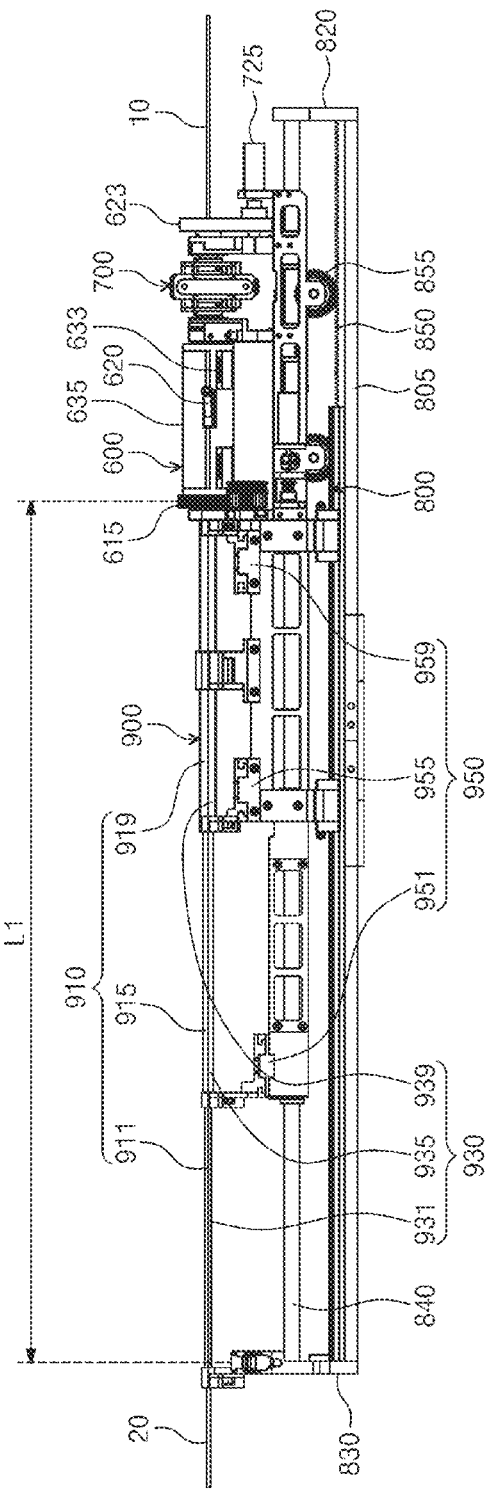
[Fig. 30]

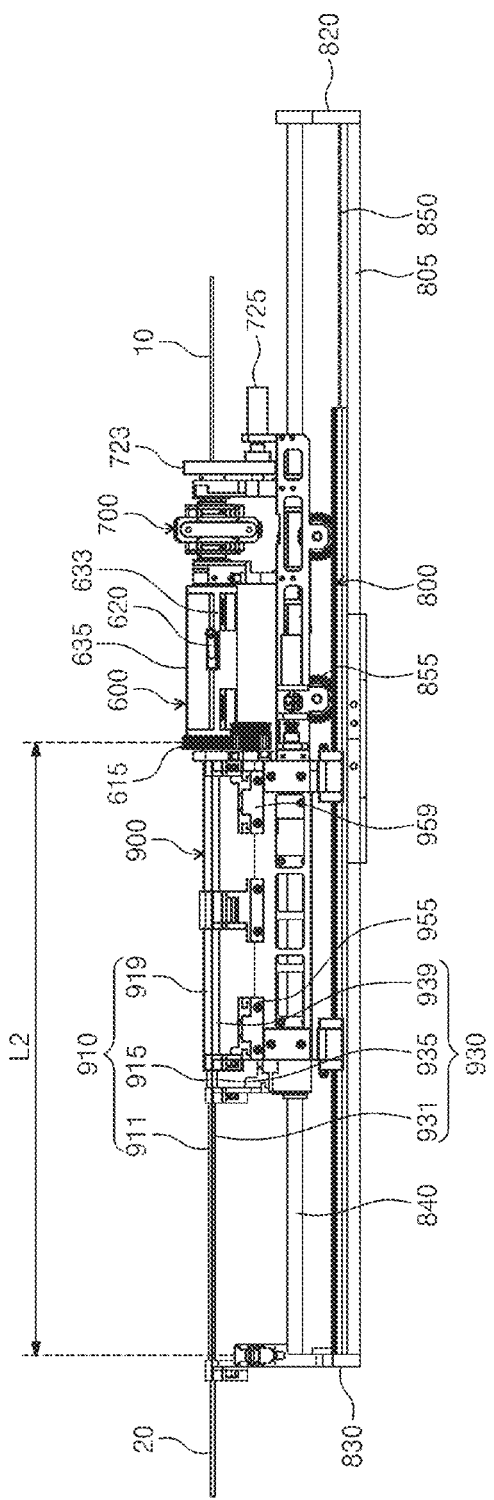
[Fig. 31]

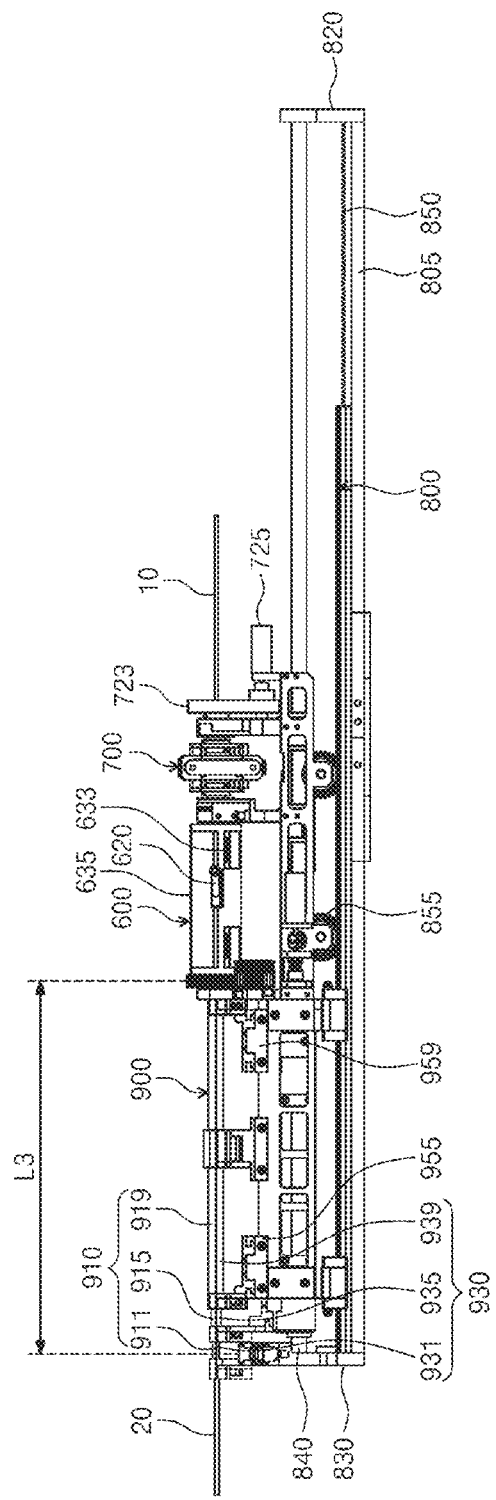
[Fig. 32]

[Fig. 33]
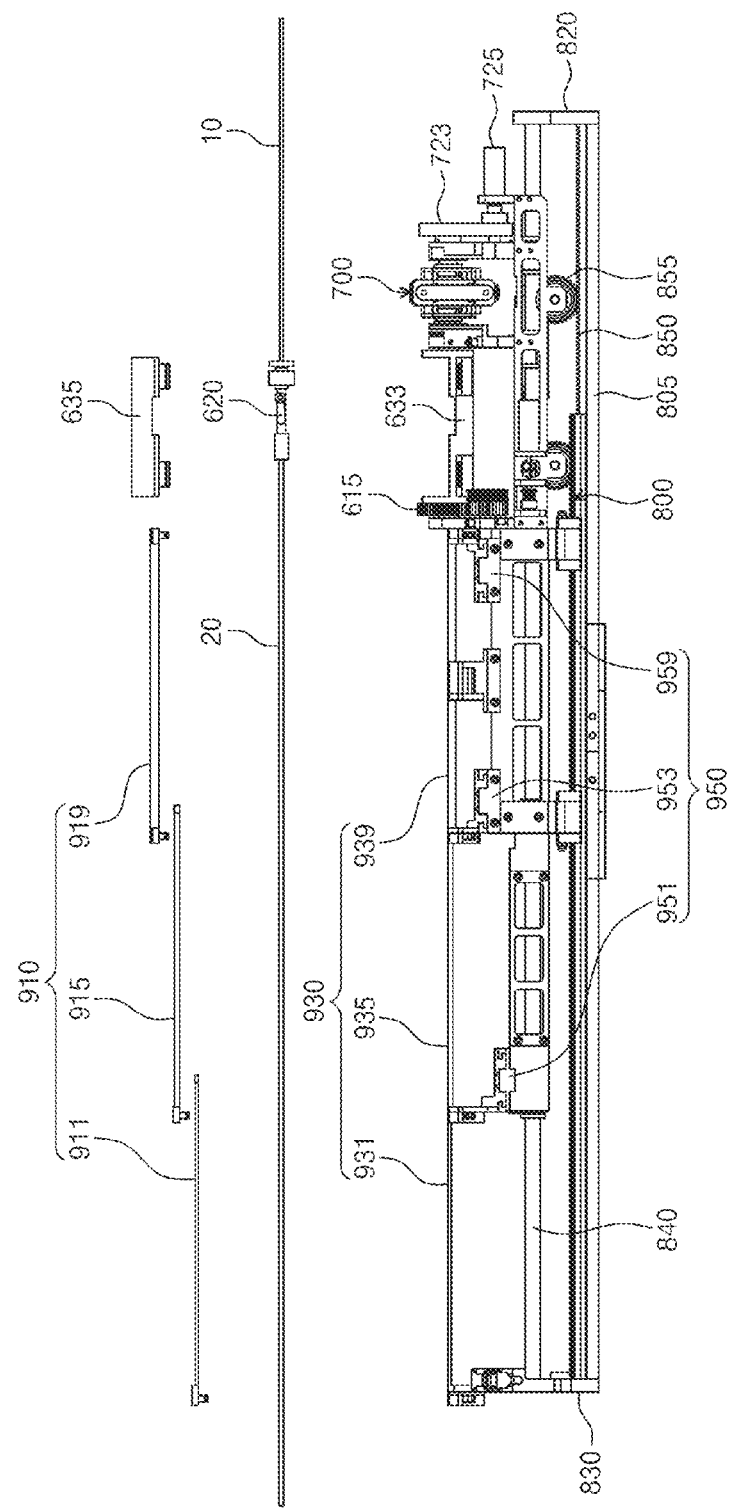

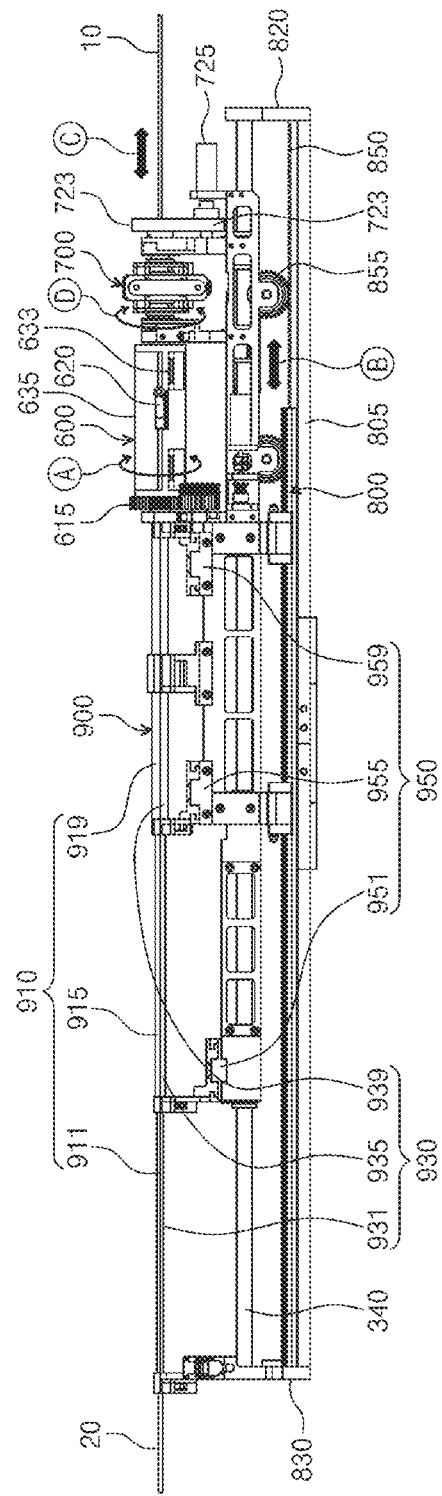
[Fig. 34]

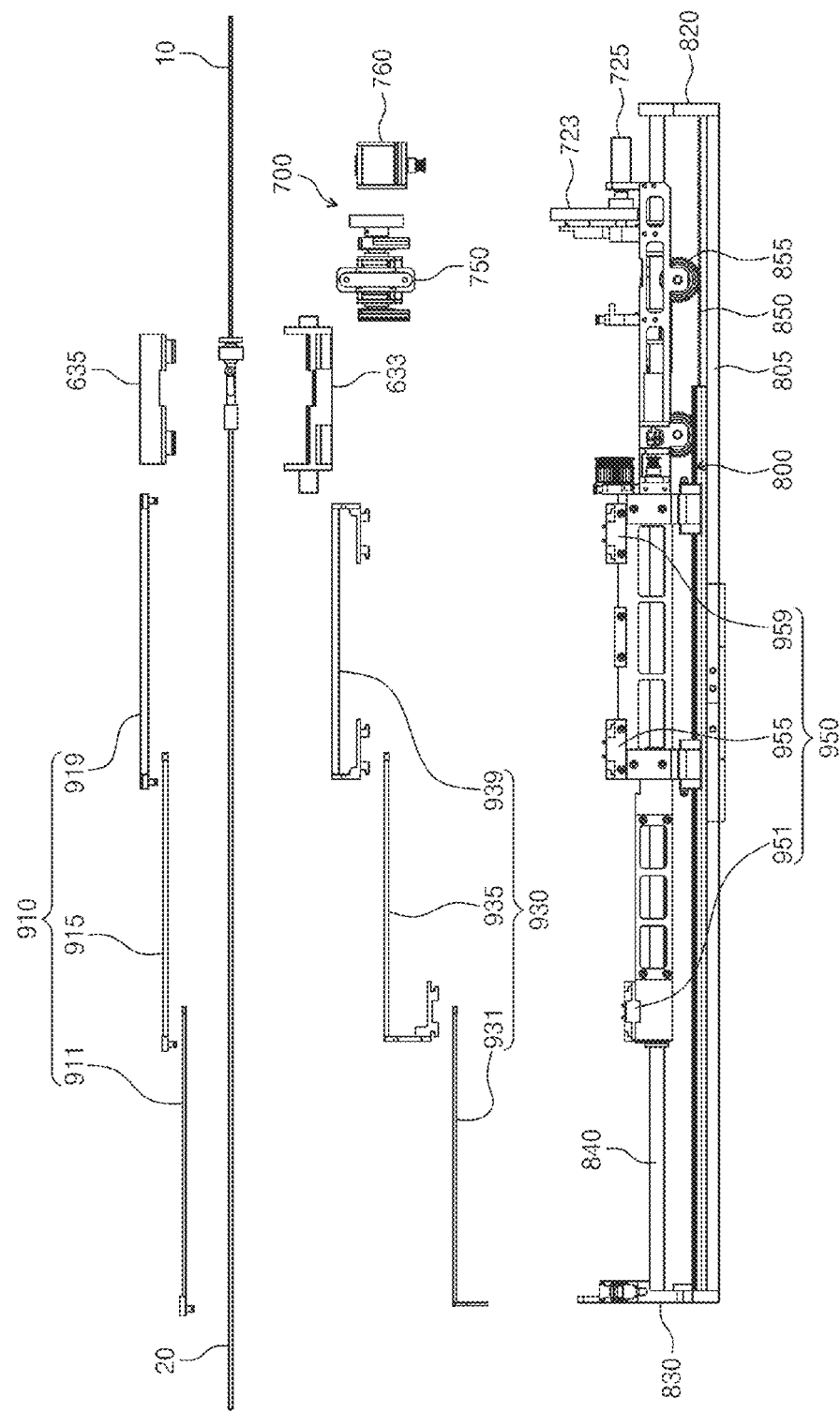
[Fig. 35]

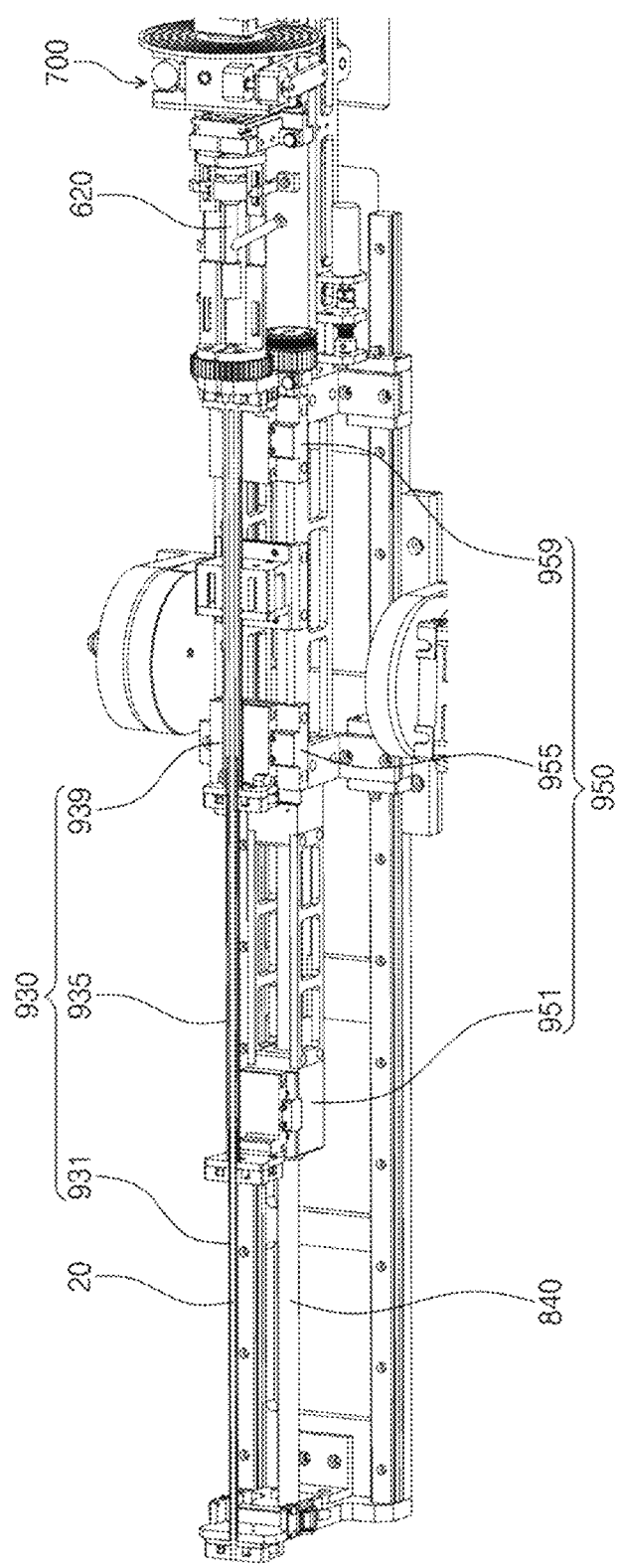
[Fig. 36]

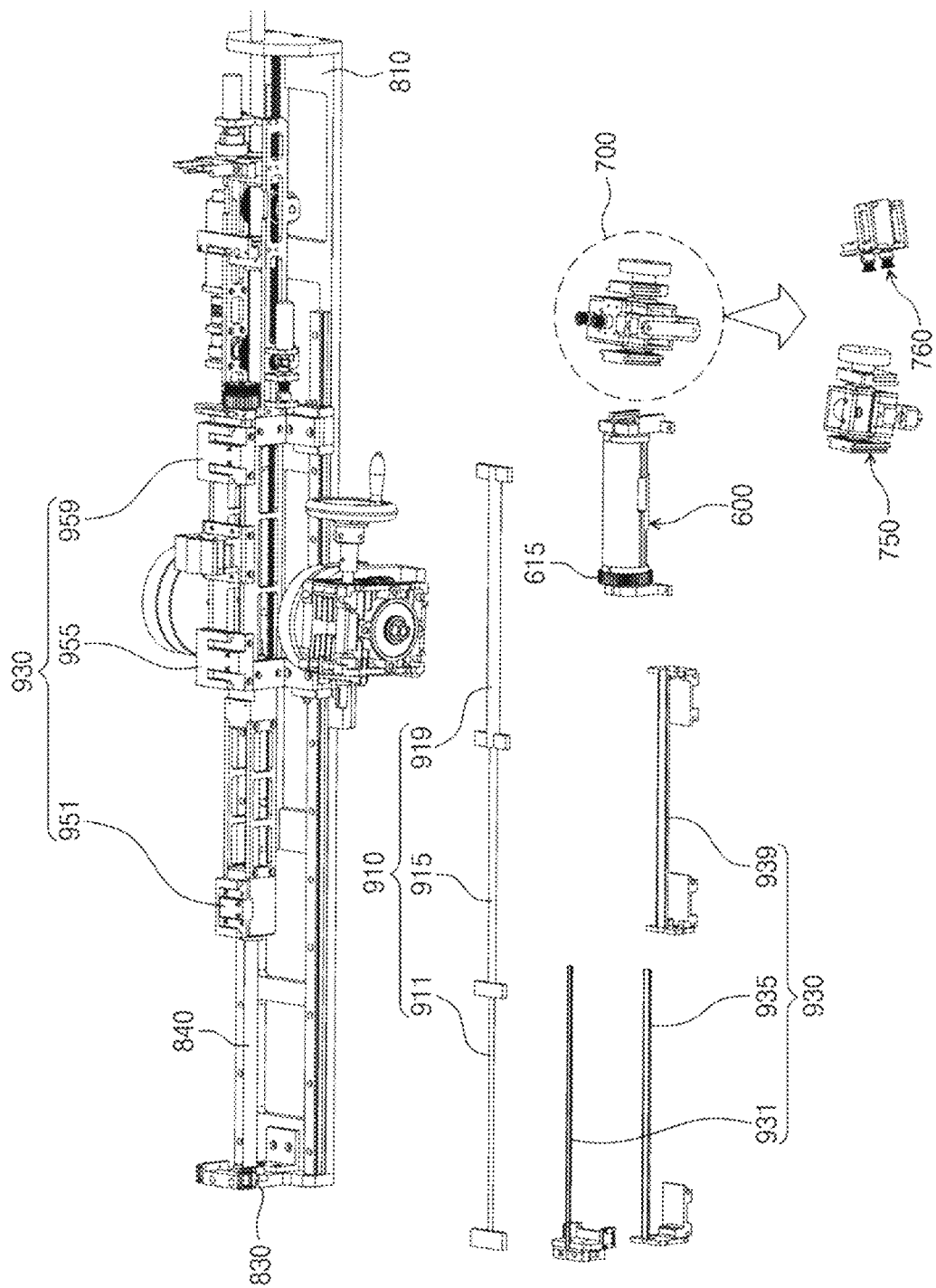
[Fig. 37]

[Fig. 38]
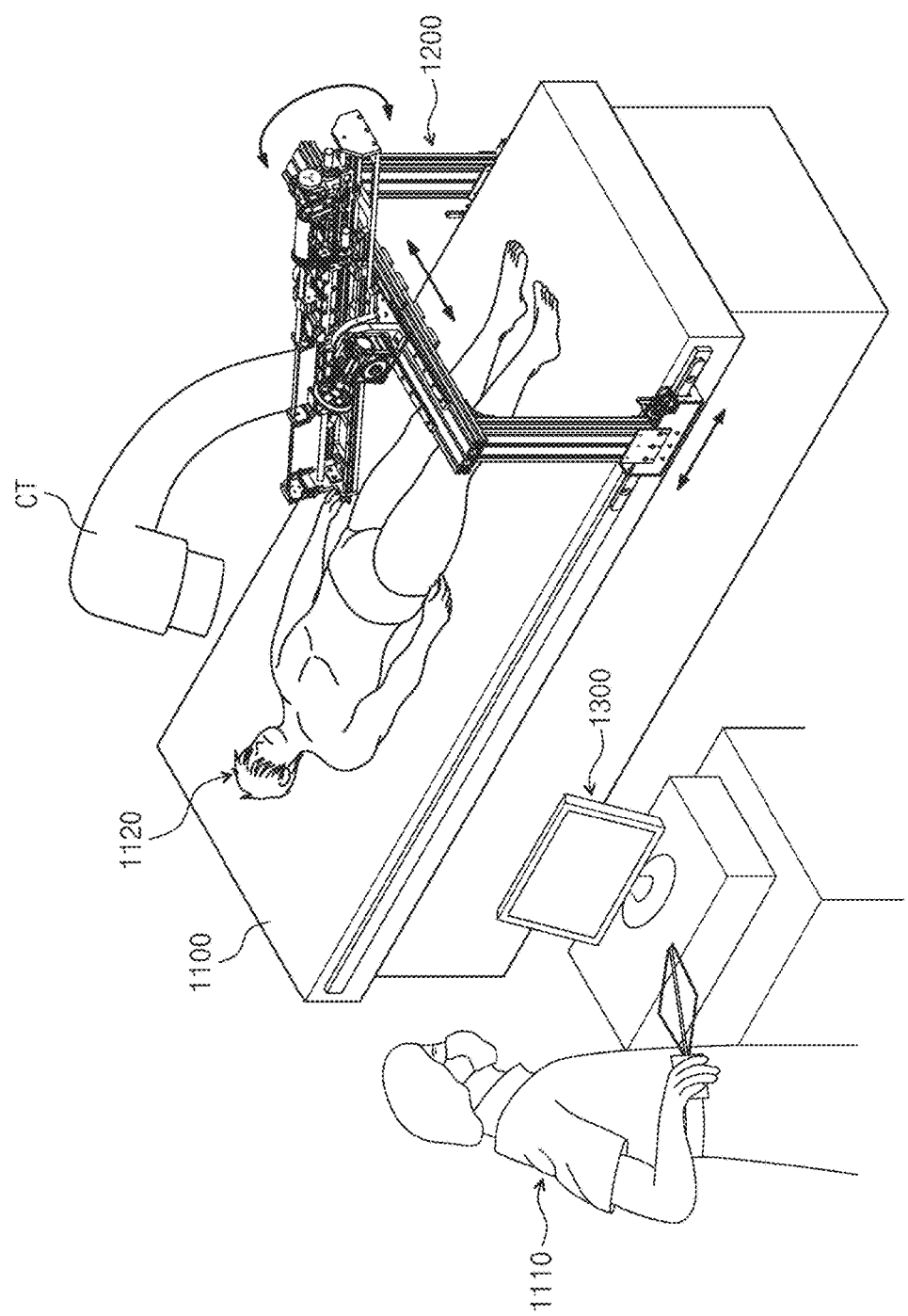

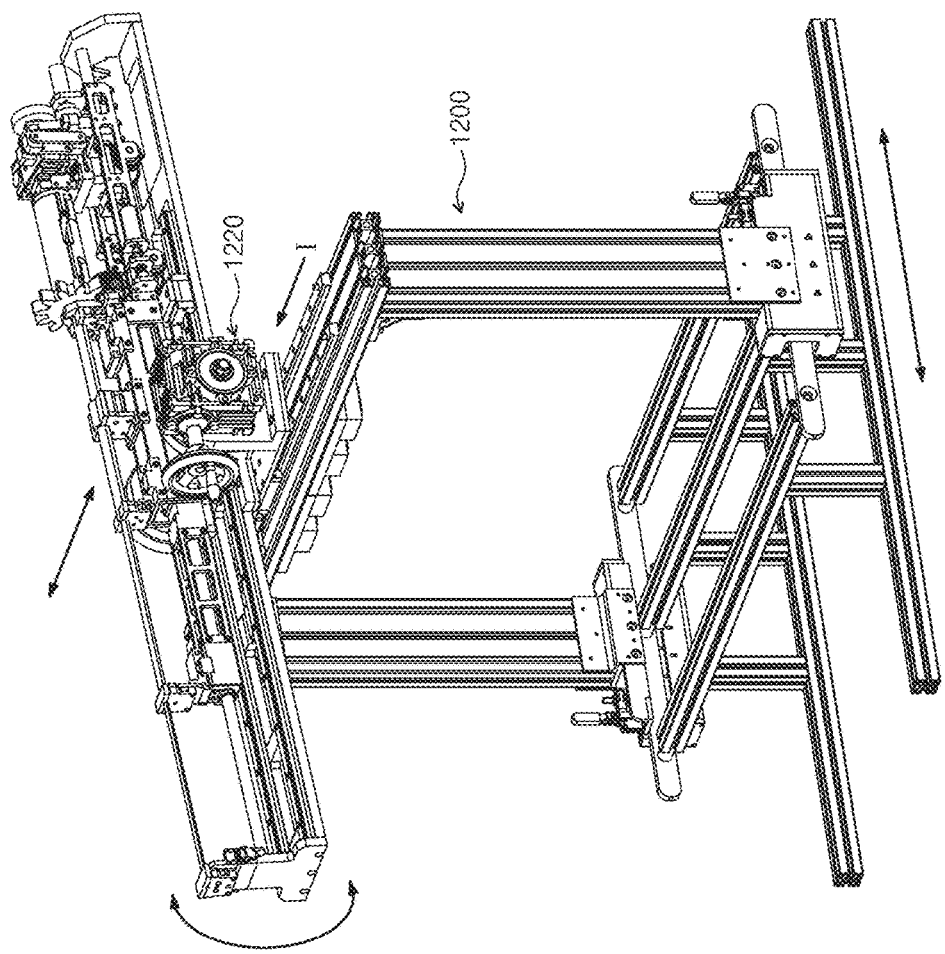
[Fig. 39]

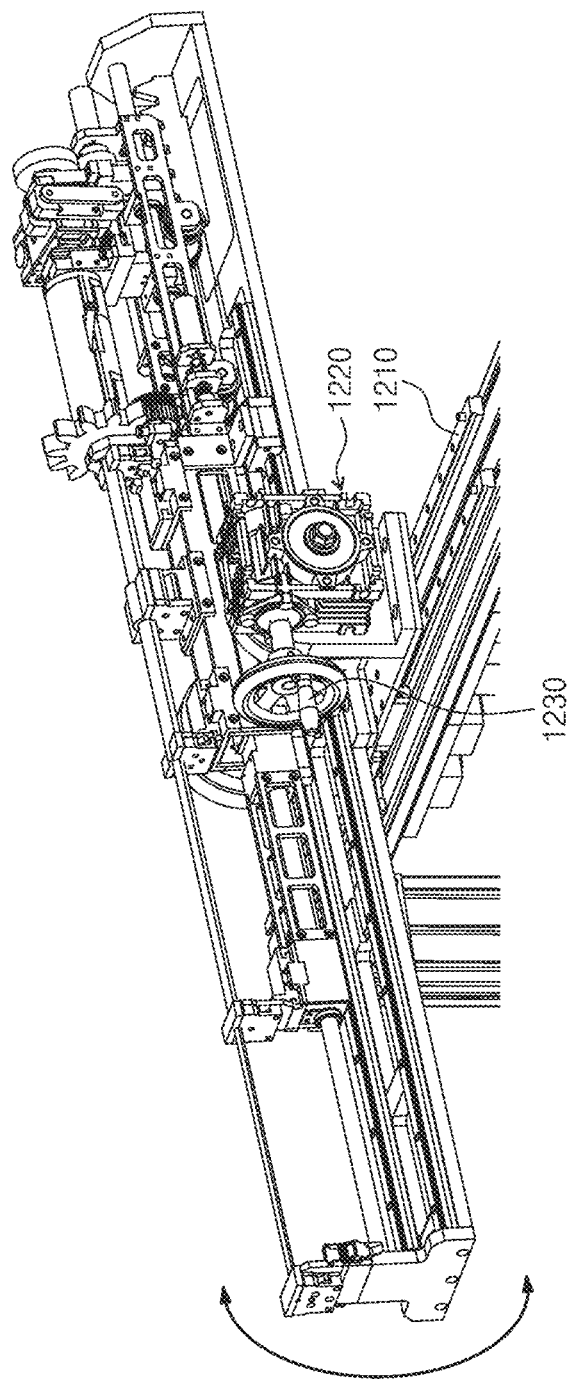
[Fig. 40]

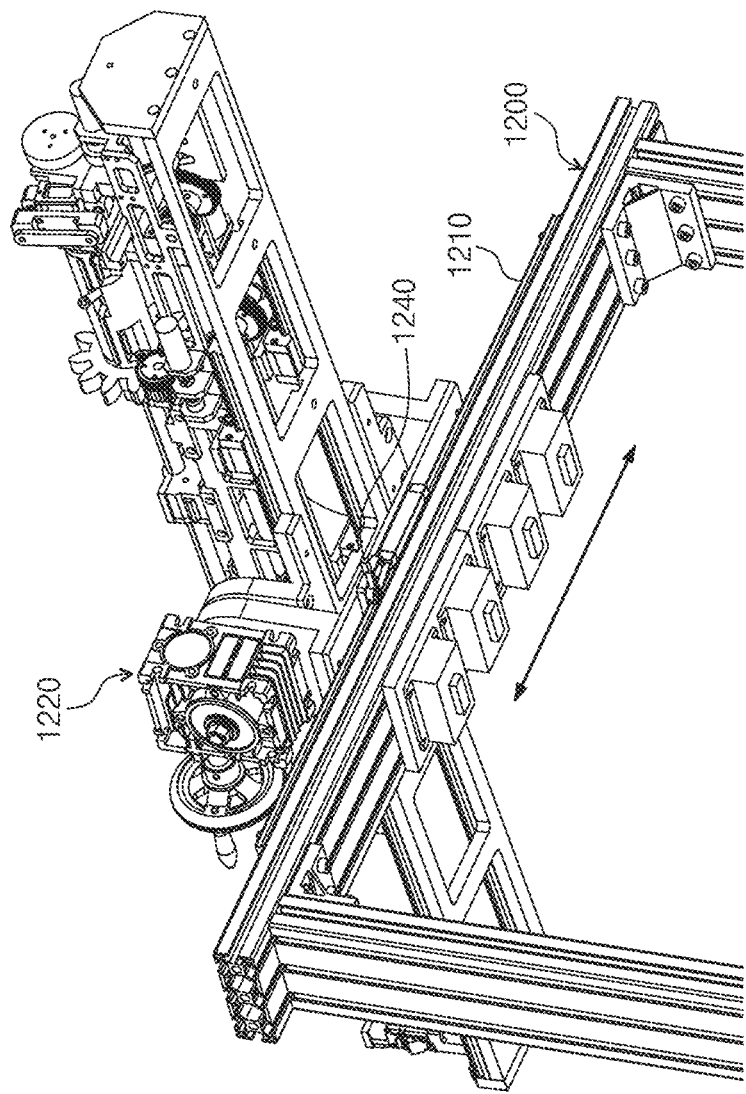
[Fig. 41]

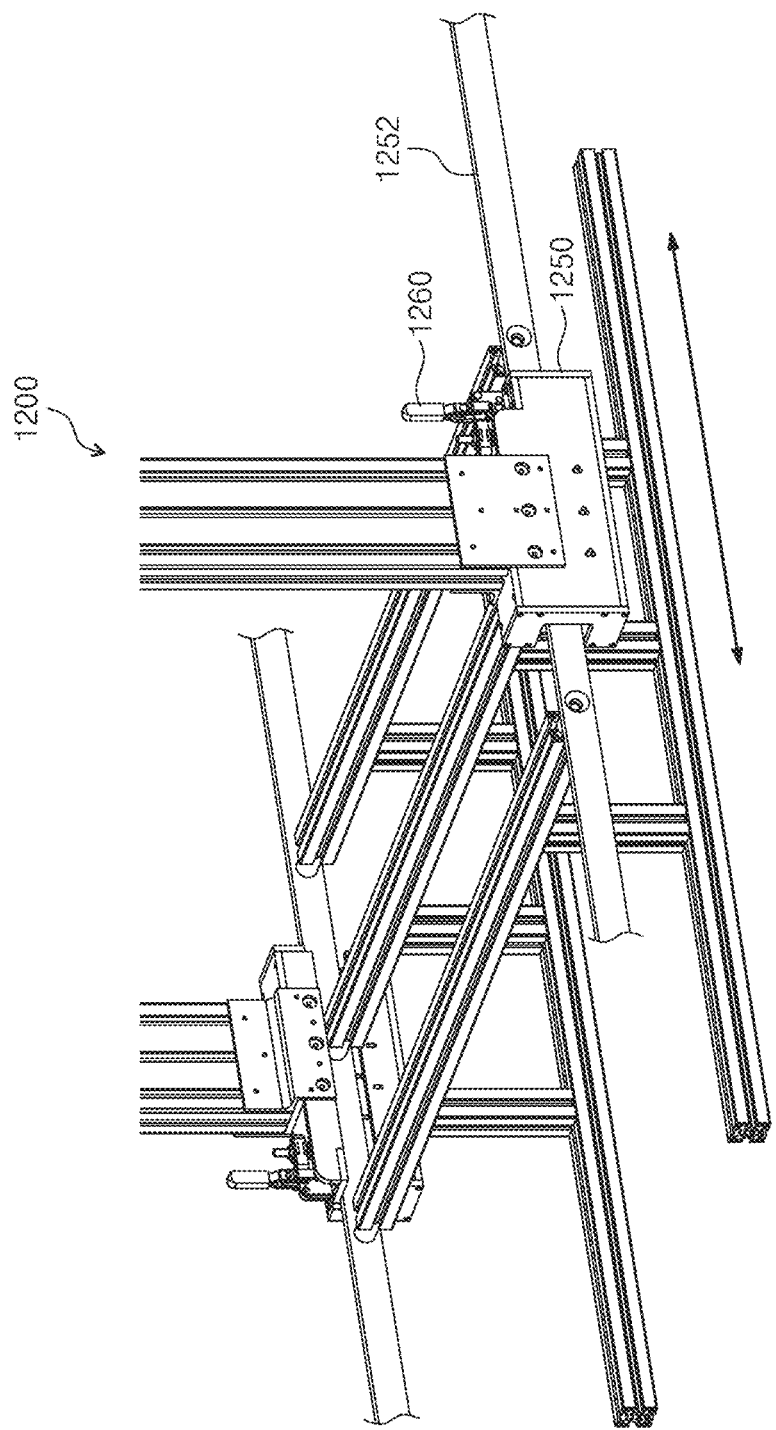
[Fig. 42]

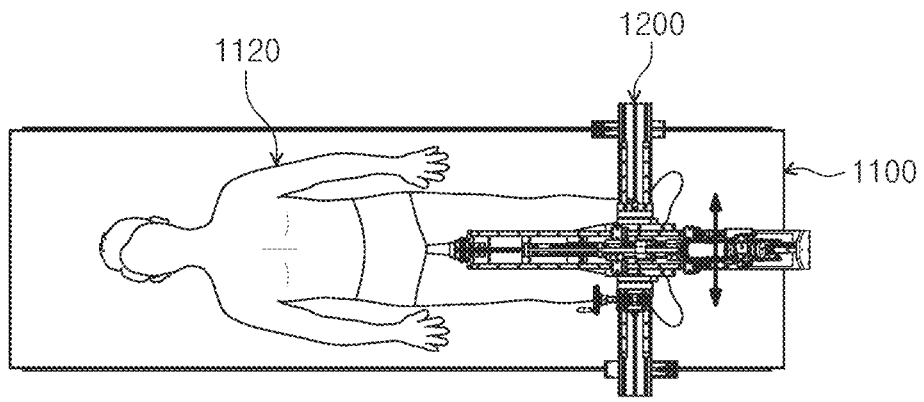
[Fig. 43 a]
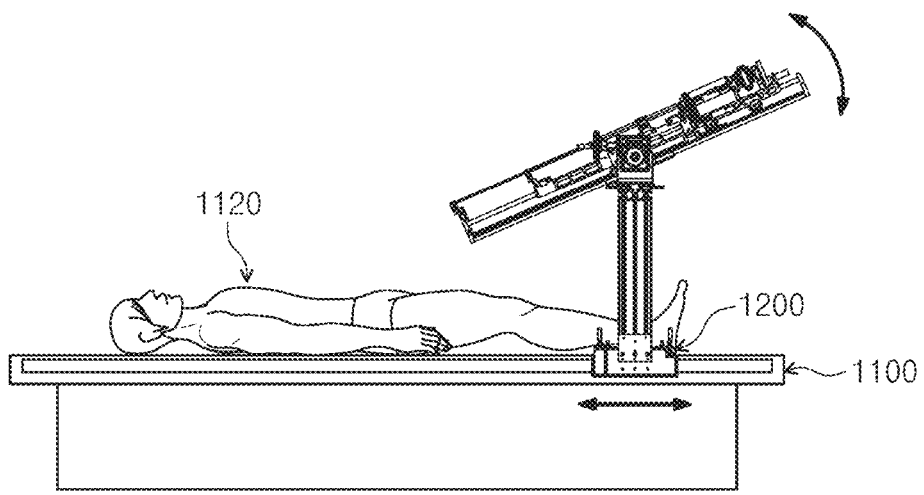
[Fig. 43b]

VASCULAR INTERVENTION ROBOT AND VASCULAR INTERVENTION SYSTEM

CROSS-REFERENCE TO RELATED APPLICATION

This application is a continuation of pending International Application No. PCT/KR2016/005857, which was filed on Jun. 2, 2016 and claims priority to Korean Patent Application Nos. 10-2015-0085253 and 10-2015-0089044, filed on Jun. 16, 2015 and Jun. 23, 2015, in the Korean Intellectual Property Office, the disclosures of which are hereby incorporated by reference in their entireties.

BACKGROUND

1. Field

Embodiments of the inventive concepts relate to a vascular intervention robot and a vascular intervention system and, more particularly, to a vascular intervention robot and a vascular intervention system, which facilitate disinfection and replacement of components by simplifying a detachable structure.

2. Description of the Related Art

Vascular Intervention

The vascular intervention is a minimally invasive surgery for curing vascular disease or cancer. In the vascular intervention, a small catheter having a diameter of several mm or less may be percutaneously inserted to a lesion region through a blood vessel under roentgenography to reach a target organ, and the target organ may be cured using the small catheter. Trans-arterial chemoembolization (TACE), percutaneous transluminal angioplasty and artificial vascular stent installation for aortic disease are known as representative curing methods of the vascular intervention in Korea and other countries.

In particular, liver cancer corresponds to one of main causes of death. According to the National Cancer Information Center data released in 2011, the incidence of liver cancer was lower than those of stomach cancer, thyroid cancer, colorectal cancer and lung cancer in both men and women. However, a death rate by the liver cancer was lower than a death rate by the lung cancer but was the second highest in both men and women. The liver cancer may be completely cured by surgical resection, but advanced liver cancer which may not be completely cured may be cured by the TACE.

In the TACE, the artery nourishing the liver cancer is searched, an anticancer drug is injected into the artery, and then, the artery is blocked (see FIG. 1). In more detail, the femoral artery located in the groin is punctured with a needle, and a wire and a catheter (see FIG. 2) are inserted through the punctured femoral artery to approach an origin region of the hepatic artery (see FIG. 3). Thereafter, a contrast image of the hepatic artery is obtained while injecting a vascular contrast medium. Necessary information for treatment (e.g., a position and a size of a cancer and a blood supply aspect) is obtained through the contrast image. Thus, a kind and a capacity of a suitable anticancer drug or embolic material are determined based on the obtained information. When a treatment method is determined, a micro-catheter having a diameter of about 3 F (1 F=0.33 mm) is inserted to the origin region to treat the cancer. A treatment time may range from about 1 hour to 2 hours but may be changed depending on a branch aspect of the hepatic artery of a patient and a complexity of a arterial branch distribution of a cancer.

Need for Vascular Intervention Robot

As shown in FIG. 4, a blood vessel may be divided into several branches or may have a curved shape. Thus, to prevent a blood vessel from being damaged, the vascular intervention uses an insert having several diameters, called a co-axial system of a catheter and a guide wire. At this time, since the blood vessel has a branch point of the branches or a curved portion, an operator should manually and precisely steer the catheter and the guide wire along a direction of the blood vessel. Since high precision is required, a treatment time increases. Thus, the operator is exposed to radiation during the vascular intervention for a long time. In particular, since the operator may be exposed to the radiation several times a day, a system for reducing the radiation exposure of the operator should be prepared.

Thus, it is necessary to develop a master-slave type system that can remotely control a surgical tool to avoid radiation exposure.

In addition, since a catheter and a guide wire used in a slave apparatus are exposed to various contamination environments, the master-slave type system should be designed to easily disinfect a component surrounding the catheter and the guide wire.

The inventors invented or suggested the present invention to solve conventional problems described above.

SUMMARY

Embodiments of the inventive concepts may provide semi-automatic vascular intervention robot which uses existing surgical tools, automatically performs procedure(s) in which radiation exposure is great, and manually performs other procedure(s).

Embodiments of the inventive concepts may also provide a vascular intervention robot having a structure in which a component is easily attachable and detachable.

Embodiments of the inventive concepts may further provide a vascular intervention system with a high degree of freedom.

In an aspect, a vascular intervention robot may include a catheter rotation unit for rotating a catheter on an axis parallel to a longitudinal direction of the catheter; a guide wire rotation and supply unit that is provided at one side of the catheter rotation unit and that is provided for transferring a guide wire in a longitudinal direction of the guide wire and for rotating the guide wire on an axis parallel to the longitudinal direction of the guide wire in a state in which the guide wire is inserted in the catheter; a transfer unit for transferring the catheter rotation unit and the guide wire rotation and supply unit in the longitudinal direction of the catheter; and an expanding and contracting unit that is provided at another side of the catheter rotation unit and that is expandable and contractible along the longitudinal direction of the catheter while supporting the catheter when the transfer unit transfers the catheter rotation unit and the guide wire rotation and supply unit in the longitudinal direction of the catheter.

In some embodiments, a Y-connector may be coupled to the catheter rotation unit. The Y-connector may include a body having a pipe shape, and a branch portion having a pipe shape and coupled to the body between one end and another end of the body so as to be connected to an inside of the body. The catheter may be fixed at the one end of the body, and the guide wire may be inserted into the body from the another end of the body and may be inserted into the catheter at the one end of the body. A fluid is injected into the branch portion.

In some embodiments, the catheter rotation unit may include a pad being in contact with top and bottom portions of the Y-connector to fix the Y-connector.

In some embodiments, the guide wire rotation and supply unit may include a guide wire supply unit including: two rollers facing each other; and a roller driving unit driving at least one of the two rollers. The guide wire may be inserted between the two rollers and may be transferred in the longitudinal direction of the guide wire when the two rollers are driven by the roller driving unit.

In some embodiments, the guide wire rotation and supply unit may further include a guide wire rotation unit including: a guide wire rotor supporting the rollers and the roller driving unit; and a guide wire driver rotating the guide wire rotor on the axis parallel to the longitudinal direction of the guide wire.

In some embodiments, the vascular intervention robot may further include a support part including: a base part having a flat plate shape; a first partition provided at one end of the base part; a second partition provided at another end of the base part; and a support bar extending from the first partition to the second partition.

In some embodiments, the catheter rotation unit and the guide wire rotation and supply unit may be disposed on the transfer unit, and the transfer unit may move in the longitudinal direction of the catheter on the base part by rack and pinion. A first insertion hole in which the support bar is inserted may be provided in the transfer unit, and the transfer unit may move along the support bar when the transfer unit moves on the base part.

In some embodiments, the expanding and contracting unit may include a plurality of tubular structures continuously provided from the another side of the catheter rotation unit to support the catheter. An $N^{th}$ tubular structure from the another side of the catheter rotation unit may slide inside and outside an $N-1^{th}$ tubular structure or $N+1^{th}$ tubular structure from the another side of the catheter rotation unit, such that the expanding and contracting unit may be expandable and contractible in the longitudinal direction of the catheter.

In some embodiments, the expanding and contracting unit may include a plurality of tubular structures continuously provided from the another side of the catheter rotation unit to support the catheter, and a plurality of supporters supporting the plurality of tubular structures, respectively. An end of the tubular structure farthest from the another end of the catheter rotation unit may be fixed at the second partition. A second insertion hole in which the support bar is inserted may be provided in at least one of the plurality of supporters, and the supporter having the second insertion hole may move along the support bar when the transfer unit moves on the base part.

In some embodiments, each of the tubular structures may include a support structure supporting the catheter; and a cover which is coupled to an upper side of the support structure and is detachable.

In another aspect, a vascular intervention robot may include a catheter rotation unit for rotating a catheter extending in a longitudinal direction on an axis parallel to the longitudinal direction; a guide wire rotation and supply unit for rotating a guide wire inserted in the catheter on the same axis as the catheter; a catheter guide unit supporting the catheter and folding when the catheter is transferred in the longitudinal direction, the catheter guide unit including a catheter cover covering an upper portion of the catheter and a catheter support part supporting a lower portion of the catheter; and a mount part on which the catheter guide unit is mounted. The catheter cover and the catheter support part of the catheter guide unit may be detachable from the mount part.

In some embodiments, the catheter cover may include a fixing wing provided at one end of the catheter cover and coupled to the catheter support part.

In some embodiments, the catheter support part may include a fixing plate fixing the catheter support part to the mount part, and the fixing plate may include a fitting part extending in a direction different from the longitudinal direction of the catheter.

In some embodiments, the mount part may include a receiving groove receiving the fitting part, and the receiving groove may extend in a direction different from the longitudinal direction of the catheter.

In some embodiments, the mount part may include a fixing pin preventing the fitting part from escaping in a state in which the fitting part of the catheter support part is inserted and fixed in the receiving groove of the mount part.

In some embodiments, the catheter rotation unit, the guide wire rotation and supply unit and the catheter guide unit, which are in contact with at least one of the catheter and the guide wire, may be detachable.

In some embodiments, the guide wire rotation and supply unit may include a guide roller part transferring the guide wire; and a roller driving unit providing driving force to the guide roller part. The guide roller part and the roller driving unit may be detachable from the vascular intervention robot.

In still another aspect, a vascular intervention system may include the vascular intervention robot described above; and a frame fixing the vascular intervention robot in such a way that the vascular intervention robot is movable relatively with respect to a treatment bed. The frame may include an up-and-down direction rotation unit adjusting an angle of the vascular intervention robot in up and down directions.

BRIEF DESCRIPTION OF THE DRAWINGS

FIG. 1 is a schematic view showing a liver cancer and a nourishing hepatic artery.

FIG. 2 shows images of a catheter (left) and a micro catheter-guide wire assembly (right), which are used in TACE.

FIG. 3 is a schematic view showing a state in which a guide wire having a diameter of 3 F to 4 F is inserted within an insertion catheter having a diameter of 6 F to 7 F.

FIG. 4 is an image showing an example of hepatic arterial chemoembolization.

FIG. 5 is a conceptual view showing an entire mechanism of a vascular intervention robot according to a first embodiment of the inventive concepts.

FIG. 6 is a side view showing the vascular intervention robot according to the first embodiment of the inventive concepts.

FIG. 7 is an enlarged perspective view showing a telescope structure of the vascular intervention robot of FIG. 6.

FIG. 8 is an enlarged perspective view showing a catheter rotation unit of the vascular intervention robot of FIG. 6.

FIG. 9 is an enlarged perspective view showing a roller mechanism (i.e., a guide wire rotation and supply unit) of the vascular intervention robot of FIG. 6.

FIG. 10 is an exploded perspective view showing the vascular intervention robot according to the first embodiment of the inventive concepts.

FIG. 11 is a combined perspective view showing the vascular intervention robot according to the first embodiment of the inventive concepts.

FIG. 12 is a side view showing the vascular intervention robot according to the first embodiment of the inventive concepts.

FIG. 13 is a plan view showing a Y-connector and a catheter rotor of FIG. 10.

FIG. 14 is a cross-sectional view showing the Y-connector and the catheter rotor of FIG. 10.

FIGS. 15A to 15C are side views showing a process of operating an expanding and contracting unit of the vascular intervention robot according to the first embodiment of the inventive concepts.

FIGS. 16A, 16B and 17 to 19 are side views showing a process of operating the vascular intervention robot according to the first embodiment of the inventive concepts.

FIG. 20 is a perspective view showing a vascular intervention robot according to a second embodiment of the inventive concepts.

FIG. 21 is a side view showing the vascular intervention robot according to the second embodiment of the inventive concepts.

FIG. 22 is a plan view showing the vascular intervention robot according to the second embodiment of the inventive concepts.

FIG. 23 is a perspective view showing a Y-connector according to the second embodiment of the inventive concepts.

FIGS. 24A and 24B are perspective views showing a guide wire rotation and supply unit according to the second embodiment of the inventive concepts.

FIGS. 25A to 25C, 26A to 26C and 27 are perspective views showing a catheter guide unit according to the second embodiment of the inventive concepts.

FIG. 28 is a perspective view showing a mount part according to the second embodiment of the inventive concepts.

FIG. 29 is a perspective view showing a process of assembling the catheter guide unit according to the second embodiment of the inventive concepts.

FIGS. 30 to 32 are views showing a method of driving the catheter guide unit according to the second embodiment of the inventive concepts.

FIGS. 33 and 35 are views showing a method of driving the vascular intervention robot according to the second embodiment of the inventive concepts.

FIGS. 36 and 37 are images showing the vascular intervention robot according to the second embodiment of the inventive concepts.

FIG. 38 is a view showing a vascular intervention system according to an embodiment of the inventive concepts.

FIGS. 39 to 43 are views showing a vascular intervention system according to an embodiment of the inventive concepts in detail.

DETAILED DESCRIPTION OF THE EMBODIMENTS

The inventive concepts will now be described more fully hereinafter with reference to the accompanying drawings, in which exemplary embodiments of the inventive concepts are shown. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts.

It will be understood that when an element such as a layer, region or substrate is referred to as being "on" another element, it can be directly on the other element or intervening elements may be present. In addition, in the drawings, the thicknesses of layers and regions are exaggerated for clarity.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concepts explained and illustrated herein include their complementary counterparts. As used herein, the term "and/or" includes any and all combinations of one or more of the associated listed items.

The terminology used herein is for the purpose of describing particular embodiments only and is not intended to limit the invention. As used herein, the singular terms "a", "an" and "the" are intended to include the plural forms as well, unless the context clearly indicates otherwise. It will be further understood that the terms "comprises", "comprising", "includes", "including", "have", "has" and/or "having" when used herein, specify the presence of stated features, integers, steps, operations, elements, and/or components, but do not preclude the presence or addition of one or more other features, integers, steps, operations, elements, components, and/or groups thereof. Furthermore, it will be understood that when an element is referred to as being "connected" or "coupled" to another element, it may be directly connected or coupled to the other element or intervening elements may be present.

In addition, in explanation of the present invention, the descriptions to the elements and functions of related arts may be omitted if they obscure the subjects of the inventive concepts.

Analysis of Vascular Intervention and Development of Vascular Intervention Robot FIG. 5 shows an entire process of the vascular intervention. A guide wire is inserted, and a catheter is inserted through the guide wire. At this time, the guide wire and the catheter have a degree of freedom with respect to insertion and rotation. Among these processes, processes in which radiation exposure occurs correspond to only third and sixth processes, and thus a developing robot system may remotely control the third and sixth processes and a medical doctor may perform other processes. Therefore, an entire system may be simplified and existing surgical tools (e.g., the catheter) may be used.

A vascular intervention robot according to a first embodiment of the inventive concepts will be described hereinafter.

Vascular Intervention Robot

Since the guide wire and the catheter should be inserted and rotated, the vascular intervention robot needs 4 degrees of freedom. FIG. 6 shows a mechanism of a catheter driven in 4 degrees of freedom. A three-stage telescope structure was designed to realize co-axial motion of the guide wire and the catheter. This telescope structure prevents the guide wire and the catheter from sagging. To easily attach or install an existing surgical tool to the robot by a medical doctor, the telescope structure was designed in such a way that lower and upper components are vertically separated from each other and then the upper component is assembled with the lower component to cover the catheter after the catheter is located on the lower component (see FIG. 7). This separate assembly design has the advantage in disinfection.

The catheter and a surgical tool (i.e., a Y-connector) are fixed at an end of the telescope in a catheter rotation unit of FIG. 8. Insertion of the catheter is driven while folding the telescope structure by a rack and pinion mechanism located at a base of the robot. Rotation of the catheter is driven by rotating the whole of the catheter rotation unit by a motor engaged with the catheter rotation unit by using gears.

The guide wire is fixed at a guide wire rotation and supply unit located behind a catheter fixing part of FIG. 9. In more detail, the guide wire rotation and supply unit fixes the guide wire by friction between two rollers which are in contact with each other by a spring. In addition, insertion of the guide wire is driven by the friction of the rollers (see FIG. 9). Rotation of the guide wire is driven by rotating the whole of the roller mechanism by a motor engaged with the roller mechanism by using gears.

The vascular intervention robot according to the embodiment of the inventive concepts was actually manufactured. A size of the manufactured vascular intervention robot was about 160(W) mm×1170(L) mm×260(H) mm, and a stroke of the catheter was 425 mm.

Hereinafter, the vascular intervention robot according to the first embodiment of the inventive concepts will be described in more detail with reference to the accompanying drawings.

FIG. 10 is an exploded perspective view showing the vascular intervention robot according to the first embodiment of the inventive concepts, and FIG. 11 is a combined perspective view showing the vascular intervention robot according to the first embodiment of the inventive concepts. FIG. 12 is a side view showing the vascular intervention robot according to the first embodiment of the inventive concepts. The vascular intervention robot of FIGS. 10 to 12 will be described with further reference to FIGS. 13, 14 and 15A to 15.

As shown in FIGS. 10 to 12, the vascular intervention robot according to the present embodiment may include: a catheter rotation unit 100 for rotating a catheter 20 on an axis parallel to a longitudinal direction of the catheter 20; a guide wire rotation and supply unit 200 that is provided at one side of the catheter rotation unit 100 and that is provided for transferring a guide wire 10 in a longitudinal direction of the guide wire 10 and for rotating the guide wire 10 on an axis parallel to the longitudinal direction of the guide wire 10 in a state in which the guide wire 10 is inserted in the catheter 20; a transfer unit 300 for transferring the catheter rotation unit 100 and the guide wire rotation and supply unit 200 in the longitudinal direction of the catheter 20; and an expanding and contracting unit 400 that is provided at another side of the catheter rotation unit 100 and that is expandable and contractible along the longitudinal direction of the catheter 20 while supporting the catheter 20 when the transfer unit 300 transfers the catheter rotation unit 100 and the guide wire rotation and supply unit 200 in the longitudinal direction of the catheter 20.

The vascular intervention robot according to the present embodiment may basically perform a function of remotely controlling the catheter 20 and the guide wire 10 inserted in the catheter 20 and may include the catheter rotation unit 100, the guide wire rotation and supply unit 200, the transfer unit 300, and the expanding and contracting unit 400.

Catheter Rotation Unit

The catheter rotation unit 100 may perform a function of rotating the catheter 20. Here, the catheter rotation unit 100 may include a cylindrical catheter rotor 130, and a catheter driver 110 (e.g., a motor) that is connected to the catheter rotor 130 through gears 115 to rotate the catheter rotor 130. At this time, a Y-connector 120 is coupled in the catheter rotor 130. The Y-connector 120 may include a body 123 and a branch portion 125 (see FIG. 13). In detail, the body 123 has a pipe shape, and the catheter 20 is fixed at one end of the body 123. The guide wire 10 is inserted from another end of the body 123 into the body 123 and then is inserted into the catheter 20 at the one end of the body 123. In addition, the branch portion 125 may have a pipe shape and may be coupled between the one end and the another end of the body 123. An inner space of the branch portion 125 may be connected to an inner space of the body 123, and a fluid such as contrast media may be injected into the branch portion 125. Since the catheter 20 is fixed at the Y-connector 120, the catheter 20 may be rotated on the axis parallel to the longitudinal direction of the catheter 20 when the Y-connector 120 coupled in the catheter rotor 130 is rotated together with the catheter rotor 130. In more detail, as shown in FIG. 10, the catheter rotor 130 may include a rotation body 133 and a rotation cover 135 which is coupled to an upper side of the rotation body 133 and is detachable. Thus, when the rotation cover 135 is coupled to the rotation body 133 after the Y-connector 120 is located in the rotation body 133, the Y-connector 120 can be coupled in the catheter rotor 130. When the rotation cover 135 is detached from the rotation body 133 as needed, the Y-connector 120 may be detached from the catheter rotor 130. Additionally, as shown in FIG. 14, a pad 137 formed of urethane or the like may be provided in the inside of the rotation body 133 and the rotation cover 135. The pad 137 may be in contact with top and bottom portions of the Y-connector 120 to firmly couple the Y-connector 120 to the catheter rotor 130. Meanwhile, the Y-connector 120 may be an existing surgical tool. Since the existing surgical tool is used, a total cost may be reduced.

Guide Wire Rotation and Supply Unit

The guide wire rotation and supply unit 200 (see FIG. 10) may perform functions of transferring and rotating the guide wire 10. Here, the guide wire rotation and supply unit 200 may include a guide wire supply unit 210 for transferring the guide wire 10, and a guide wire rotation unit 220 for rotating the guide wire 10.

In detail, the guide wire supply unit 210 may include two rollers 211 facing each other and being in contact with each other, and a roller driving unit 213 (e.g., a motor) for driving at least one of the two rollers 211. Here, the guide wire 10 may be inserted between the two rollers 211 and may be transferred in the longitudinal direction of the guide wire 10 when the two rollers 211 are driven by the roller driving unit 213. In addition, even though driving force of the roller driving unit 213 is provided to only one of the two rollers 211, the two rollers 211 may be rotated together since the two rollers 211 are in contact with each other by elasticity of a spring, thereby transferring the guide wire 10 inserted therebetween.

The guide wire rotation unit 220 may include a guide wire rotor 221 supporting the rollers 211 and the roller driving unit 213, and a guide wire driver 225 (e.g., a motor) connected to the guide wire rotor 221 through gears 223 to rotate the guide wire rotor 221 on the axis parallel to the longitudinal direction of the guide wire 10. Thus, when the guide wire rotor 221 is rotated by the guide wire driver 225, the guide wire 10 may be rotated on the axis parallel to the longitudinal direction of the guide wire 10 in a state in which the guide wire 10 is inserted between the two rollers 211.

Transfer Unit

The transfer unit 300 may perform a function of transferring the catheter rotation unit 100 and the guide wire rotation and supply unit 200 in the longitudinal direction of the catheter 20 (or in the longitudinal direction of the guide wire 10). Here, the catheter rotation unit 100 and the guide wire rotation and supply unit 200 may be disposed on the transfer unit 300, and the transfer unit 300 may transfer the catheter rotation unit 100 and the guide wire rotation and supply unit 200 while moving relatively with respect to a support part 305. The support part 305 may include a base part 310 formed in a flat plate shape, a first partition 320 provided at one end of the base part 310, a second partition 330 provided at another end of the base part 310, and a support bar 340 extending from the first partition 320 to the second partition 330. Here, the transfer unit 300 moves in the longitudinal direction of the catheter 20 with respect to the base part 310 by rack & pinion. In detail, as shown in FIG. 11, a rack 350 may be provided on a top surface of the base part 310, and a pinion 355 may be provided at the transfer unit 300. The rack 350 of the base part 310 may be engaged with the pinion 355 of the transfer unit 300. Thus, when the pinion 355 of the transfer unit 300 receives driving force from a pinion driver 360 (e.g., a motor), the pinion 355 of the transfer unit 300 may move along the rack 350 of the base part 310. As a result, the transfer unit 300 may move along the base part 310. In addition, a first insertion hole 370 (see FIG. 12) may be provided in the transfer unit 300, and the support bar 340 may be inserted in the first insertion hole 370. Thus, the transfer unit 300 may move along the support bar 340 when the transfer unit 300 moves on the base part 310. In other words, the transfer unit 300 may move while being guided by the support bar 340.

Expanding and Contracting Unit

The expanding and contracting unit 400 may perform a function of supporting the catheter 20 while expanding and contracting along the longitudinal direction of the catheter 20. Here, the expanding and contracting unit 400 may be provided at the another side of the catheter rotation unit 100 (a side opposite to the guide wire rotation and supply unit 200) and may be formed to have a telescope structure that is entirely expandable and contractible. In detail, the expanding and contracting unit 400 may include a plurality of tubular structures 410. The tubular structures 410 may be continuously provided from the another side of the catheter rotation unit 100 to support the catheter 20. In addition, an $N^{th}$ tubular structure 410 from the another side of the catheter rotation unit 100 (where 'N' is a natural number equal to or greater than 2) may slide inside and outside an $N-1^{th}$ tubular structure 410 or an $N+1^{th}$ tubular structure 410 from the another side of the catheter rotation unit 100, and thus the expanding and contracting unit 400 may be expandable and contractible along the longitudinal direction of the catheter 20. In other words, diameters of the tubular structures 410 may sequentially decrease or increase as a distance from the catheter rotation unit 100 in one direction increases, and each of the tubular structures 410 may slide inside and outside an adjacent tubular structure 410. Thus, the expanding and contracting unit 400 can be expanded and contracted. For example, as shown in FIGS. 15A to 15C, three tubular structures 410 may be designed in such a way that diameters of the three tubular structures 410 sequentially decrease as a distance from the catheter rotation unit 100 increases. Thus, a second tubular structure 410 from the another side of the catheter rotation unit 100 may slide inside and outside a first tubular structure 410 from the another side of the catheter rotation unit 100, and a third tubular structure 410 from the another side of the catheter rotation unit 100 may slide inside and outside the second tubular structure 410 from the another side of the catheter rotation unit 100. In addition, the expanding and contracting unit 400 may include a plurality of supporters 420 supporting the plurality of tubular structures 410, respectively. Similarly to the tubular structures 410, the supporters 420 may be continuously provided from the another side of the catheter rotation unit 100, and each of the supporters 420 may slide inside and outside another supporter 420 adjacent thereto. Thus, the supporters 420 may be expandable and contractible. In detail, N supporters 420 may be provided to support the tubular structures 410, respectively, and an $N^{th}$ supporter 420 from the another side of the catheter rotation unit 100 may slide inside and outside an $N-1^{th}$ supporter 420 from the another side of the catheter rotation unit 100. However, the tubular structure 410 farthest from the another side of the catheter rotation unit 100 may not be supported by the supporter 420 but may have an end fixed at the second partition 330. In addition, a second insertion hole 425 may be provided in at least one of the supporters 420, and the support bar 340 may be inserted in the second insertion hole 425. Thus, when the transfer unit 300 moves on the base part 310, the supporter 420 having the second insertion hole 425 may move along the support bar 340. In other words, the supporter 420 may move while being guided by the support bar 340. For example, as shown in FIGS. 15A to 15C, two supporters 420 may be provided to support two tubular structures 410 (e.g., the first and second tubular structures 410 from the another side of the catheter rotation unit 100), respectively. A second supporter 420 from the another side of the catheter rotation unit 100 may slide inside and outside a first supporter 420 from the another side of the catheter rotation unit 100. In addition, an end of the third tubular structure 410 from the another side of the catheter rotation unit 100 may be fixed at the second partition 330, and the second insertion holes 425 in which the support bar 340 is inserted may be provided in the supporters 420. Thus, when the transfer unit 300 moves on the base part 310, the supporters 420 may move along the support bar 340.

Additionally, as shown in FIG. 10, the tubular structures 410 may include detachable covers 430 provided at an upper side. Thus, the catheter 20 may be located in the tubular structures 410 continuously provided, and the detachable covers 430 may be coupled to the tubular structures 410, thereby providing the catheter 20 in the tubular structures 410. In addition, when the covers 430 are detached from the tubular structures 410 as needed, the tubular structures 410 may be easily disinfected.

FIGS. 16A, 16B and 17 to 19 are side views showing a process of operating the vascular intervention robot according to the first embodiment of the inventive concepts. The process of operating the vascular intervention robot according to the first embodiment will be described with reference to FIGS. 16A, 16B and 17 to 19.

First, as shown in FIGS. 16A and 16B, the rotation cover 135 is detached from the rotation body 133, and the Y-connector 120 is located in the rotation body 133. Thereafter, the rotation cover 135 is coupled to the rotation body 133. Thus, the Y-connector 120 is coupled to the catheter rotor 130. At this time, the catheter 20 is fixed at the one end of the Y-connector 120, the guide wire 10 is inserted into the Y-connector 120 in a direction from the another end to the one end of the Y-connector 120, and then, the guide wire 10 is inserted into the catheter 20 at the one end of the Y-connector 120. In addition, the guide wire 10 is inserted between the two rollers 211 of the guide wire rotation and supply unit 200. The covers 430 are detached from the tubular structures 410, and then, the catheter 20 is located in the tubular structures 410. Thereafter, the covers 430 are coupled to the tubular structures 420 to couple the catheter 20 into the expanding and contracting unit 400. As a result, the catheter 20 and the guide wire 10 may be fixed in the vascular intervention robot according to the present embodiment, and the catheter 20 in which the guide wire 10 is inserted may be exposed outside the second partition 330.

Next, as shown in FIG. 17, the catheter rotation unit 100 may rotate the catheter rotor 130 by driving the catheter driver 110, thereby rotating the catheter 20 on the axis parallel to the longitudinal direction of the catheter 20 (see an arrow A). In addition, the transfer unit 300 may transfer the catheter rotation unit 100 and the guide wire rotation and supply unit 200 on the support part 305 by driving the pinion driver, thereby transferring the catheter 20 in the longitudinal direction of the catheter 20 (see an arrow B). In other words, the rotational motion and the longitudinal motion of the catheter 20 may be performed using the catheter rotation unit 100 and the transfer unit 300. Meanwhile, when the transfer unit 300 transfers the catheter rotation unit 100 and the guide wire rotation and supply unit 200 on the support part 305, each of the tubular structures 410 of the expanding and contracting unit 400 may support the catheter 20 while sliding inside and/or outside the adjacent tubular structure 410.

In addition, as shown in FIG. 18, the guide wire rotation and supply unit 200 may rotate the two rollers 211 by driving the roller driving unit, and thus the guide wire 10 inserted between the two rollers 211 may be transferred in the longitudinal direction of the guide wire 10 (see an arrow C). Furthermore, the guide wire rotation and supply unit 200 may rotate the guide wire rotor 221 by driving the guide wire driver 225, and thus the guide wire 10 may be rotated on the axis parallel to the longitudinal direction of the guide wire 10 (see an arrow D). In other words, the rotational motion and the longitudinal motion of the guide wire 10 may be performed using the guide wire rotation and supply unit 200.

The rotational motion and the longitudinal motion of the catheter 20 and the rotational motion and the longitudinal motion of the guide wire 10 may be sequentially performed or may be performed at the same time. As a result, the vascular intervention robot according to the present embodiment may realize 4 degrees of freedom in which rotation and insertion of the catheter 20 and the guide wire 10 can be performed.

Additionally, as shown in FIG. 19, the rotation cover 135 may be detached from the rotation body 133, and the Y-connector 120 may be separated from the rotation body 133. The separated Y-connector 120 may be replaced with new one. Furthermore, the covers 430 may be detached from the tubular structures 410, and the catheter 20 may be separated from the inside of the tubular structures 410. Thereafter, the tubular structures 410 may be easily disinfected.

The vascular intervention robot according to the first embodiment of the inventive concepts is described above with reference to FIGS. 5 to 19. Hereinafter, a vascular intervention robot according to a second embodiment of the inventive concepts will be described with reference to FIGS. 20 to 37.

FIGS. 20, 21 and 22 show a perspective view, a side view and a plan view of a vascular intervention robot according to a second embodiment of the inventive concepts, respectively. The vascular intervention robot of FIGS. 20 to 22 will be described with further reference to FIGS. 23 to 29.

The vascular intervention robot according to the second embodiment of the inventive concepts may include at least one of a catheter rotation unit 600, a guide wire rotation and supply unit 700, a transfer unit 800, and a catheter guide unit 900. In addition, the vascular intervention robot may provide rotational motion and translational motion to a catheter 20 and a guide wire 10 in a state in which the catheter 20 and the guide wire 10 are provided in a co-axial system. In the following descriptions, the catheter 20 of the second embodiment corresponds to the catheter 20 of the first embodiment, and the guide wire 10 of the second embodiment corresponds to the guide wire 10 of the first embodiment. Hereinafter, each of the components will be described.

Catheter Rotation Unit

The catheter rotation unit 600 may rotate the catheter 20 while holding the catheter 20. For example, the catheter rotation unit 600 may rotate the catheter 20 on an axis parallel to a longitudinal direction of the catheter 20. To achieve this, the catheter rotation unit 600 may include at least one of a gear 615, a Y-connector 620, a rotation body 633, and a rotation cover 635. Hereinafter, each of the components will be described.

The gear 615 may receive driving force from a catheter driver to provide rotational force for rotating the catheter rotation unit 600. The catheter driver may be, for example, a motor. In addition, the gear 615 may include a slit in which the catheter 20 is inserted in an axis direction of the gear 615.

The Y-connector 620 may be provided in a receiving space surrounded by the rotation body 633 and the rotation cover 635 and may be configured to hold the catheter 20 at one side of the Y-connector 620. This will be described in detail with reference to FIG. 23.

FIG. 23 is a perspective view showing a Y-connector according to the second embodiment of the inventive concepts.

Referring to FIG. 23, the Y-connector 620 may include a body 623 and a branch portion 625. The body 623 may have a hollow pipe shape. Thus, the catheter 20 may be inserted and held in one side of the body 623, and the guide wire 10 may be inserted in another side of the body 623. As a result, a co-axial system in which the guide wire 10 is inserted in the catheter 20 may be provided.

The branch portion 625 may have a hollow pipe shape and may be branched from the body 623. The hollow space of the branch portion 625 may be connected to the hollow space of the body 623. Thus, when a fluid (e.g., contrast media) is injected through one end of the branch portion 625, the injected fluid may be provided to the catheter 20 through the hollow spaces of the branch portion 625 and the body 623.

Referring again to FIGS. 20 to 22, the Y-connector 620 may be located in the rotation body 633. The rotation cover 635 may be provided on the rotation body 633. The rotation cover 635 may cover the Y-connector 620 and may be coupled to the rotation body 633, and thus the Y-connector 620 may be protected by the rotation cover 635.

Guide Wire Rotation and Supply Unit

Referring to FIGS. 20 to 22, the guide wire rotation and supply unit 700 may perform functions of transferring the guide wire 10 and of rotating the guide wire 10. The guide wire rotation and supply unit 700 may be provided at one side of the catheter rotation unit 600 and may receive the guide wire 10 to provide the guide wire 10 into the catheter 20 through the Y-connector 620 described above.

The guide wire rotation and supply unit 700 may receive rotation force from a guide wire driver 725 and may rotate the guide wire 10 through the gear 223. At this time, the guide wire rotation and supply unit 700 may rotate the guide wire 10 on the same axis as the catheter 20, i.e., on the axis parallel to the longitudinal direction of the catheter 20.

In addition, the guide wire rotation and supply unit 700 may hold and transfer the guide wire 10 in the longitudinal direction of the guide wire 10 by rollers (not shown) provided in the guide wire rotation and supply unit 700. This will be described in detail with reference to FIGS. 24A and 24B.

FIGS. 24A and 24B are perspective views showing a guide wire rotation and supply unit according to the second embodiment of the inventive concepts.

The guide wire rotation and supply unit 700 may include a guide roller part 750 and a roller driving unit 760. The guide roller part 750 may be provided with driving force from the roller driving unit 760 to hold and transfer the guide wire 10 in the longitudinal direction. In more detail, the guide roller part 750 may receive the guide wire 10 in an arrow direction of FIG. 24A. In addition, the guide roller part 750 may include rollers 751 and 753 facing each other. The guide wire 10 may be located between the rollers 751 and 753, and the guide wire 10 may be transferred in the longitudinal direction by relative rotation of the rollers 751 and 753 while being held by the rollers 751 and 753. At this time, at least one of the rollers 751 and 753 may be supplied with rotational force. In the present embodiment, the roller 751 is supplied with the rotational force.

The roller driving unit 760 may include a roller driver 761 that provides driving force to the guide roller part 750 to transfer the guide wire 10 in the longitudinal direction.

A rotation gear 763 may be provided at one side of the roller driver 761. A transmission gear 765 may be located at one side of the rotation gear 763 and may receive the driving force from the rotation gear 763 through a belt (not shown).

The transmission gear 765 may be engaged with the roller 751. Thus, the driving force (i.e., rotation force) generated from the roller driver 761 may be transmitted to the roller 751 through the rotation gear 763 and the transmission gear 765. Thus, the guide wire 10 located between the roller 751 and the roller 753 may be transferred in the longitudinal direction.

Transfer Unit

The transfer unit 800 may transfer the catheter rotation unit 600 and the guide wire rotation and supply unit 700 in the longitudinal direction of the catheter 20. To achieve this, the transfer unit 800 may include components related to a frame of the vascular intervention robot and components movable relatively with respect to the components related to the frame of the vascular intervention robot. In detail, the transfer unit 800 may include a base part 810, a first partition 820, a second partition 830, and a support bar 840, as the components related to the frame of the vascular intervention robot. In addition, the transfer unit 800 may include a rack 850, a pinion 855, and a pinion driver 860, as the components movable relatively with respect to the frame of the vascular intervention robot. In more detail, the base part 810 may be a frame providing a bottom surface of the vascular intervention robot. The first partition 820 and the second partition 830 may be provided at both ends of the base part 810. The support bar 840 may be provided between the first partition 820 and the second partition 830. The rack 850 may be provided on a top surface of the base part 810 in a longitudinal direction of the vascular intervention robot. The pinion 855 may be engaged with the rack 850 and may be movable by driving force provided from the pinion driver 860. Thus, the catheter rotation unit 600 and the guide wire rotation and supply unit 700 fixed on the transfer unit 800 may be movable in the longitudinal direction of the vascular intervention robot. At this time, the support bar 840 may provide a guide path of the movement of the catheter rotation unit 600 and the guide wire rotation and supply unit 700.

Catheter Guide Unit

The catheter guide unit according to the second embodiment may be another expression of the expanding and contracting unit according to the first embodiment.

The catheter guide unit 900 may support the catheter 20 while folding or telescoping in the longitudinal direction of the catheter 20. At this time, the catheter guide unit 900 may have a telescope structure for folding or telescoping. To achieve this, the catheter guide unit 900 may include a plurality of sub-catheter guide units, e.g., first, second and third sub-catheter guide units. External diameters of the first to third sub-catheter guide units may sequentially increase from the first sub-catheter guide unit to the third sub-catheter guide unit. Thus, the first sub-catheter guide unit may slide from and into the second sub-catheter guide unit in a state in which at least a portion of the first sub-catheter guide unit is inserted in the second sub-catheter guide unit, and the second sub-catheter guide unit may slide from and into the third sub-catheter guide unit in a state in which at least a portion of the second sub-catheter guide unit is inserted in the third sub-catheter guide unit.

The first to third sub-catheter guide units of which the diameters sequentially increase are described in the present embodiment for the purpose of ease and convenience in explanation. However, alternatively, diameters of the first to third sub-catheter guide units may sequentially decrease from the first sub-catheter guide unit to the third sub-catheter guide unit. In addition, three sub-catheter guide units are described for the purpose of ease and convenience in explanation. However, in other embodiments, the number of the sub-catheter guide units may be less or greater than 3.

Each of the sub-catheter guide units may include a catheter cover 910 and a catheter support part 930. The catheter support part 930 may provide a space in which the catheter 20 is located, and the catheter cover 910 may cover the catheter 20 to protect the catheter 20. As shown in FIGS. 20 to 22, the first sub-catheter guide unit may include a first catheter cover 911 and a first catheter support part 931, the second sub-catheter guide unit may include a second catheter cover 915 and a second catheter support part 935, and the third sub-catheter guide unit may include a third catheter cover 919 and a third catheter support part 939. Hereinafter, the catheter cover and the catheter support part will be described in more detail with reference to FIGS. 25A to 25C, 26A to 26C and 27.

FIGS. 25A to 25C, 26A to 26C and 27 are perspective views showing a catheter guide unit according to the second embodiment of the inventive concepts. First, the catheter cover will be described with reference to FIGS. 25A to 25C.

Referring to FIG. 25A, the first catheter cover 911 may include a body 912, a fixing wing 913, and a fixing piece 914. The body 912 may be formed to cover the catheter 20. In addition, the body 912 may include the fixing wing 913 at one side of the body 912. The fixing wing 913 may include the fixing piece 914, and the fixing piece 914 may be fitted and coupled into a fitted piece (e.g., a fixing recess) of the first catheter support part.

Referring to FIGS. 25B and 25C, the second catheter cover 915 may include a body 916, a fixing wing 917, and a fixing piece 918, and the third catheter cover 919 may include a body 920, fixing wings 921 and 923, and fixing pieces 922 and 924.

An external diameter D1 of the first catheter cover 911 may correspond to an internal diameter of the second catheter cover 915, and an external diameter D2 of the second catheter cover 915 may correspond to an internal diameter of the third catheter cover 919. Thus, the slidable telescope structure may be provided.

Hereinafter, the catheter support part will be described with reference to FIGS. 26A to 26C.

Referring to FIG. 26A, the first catheter support part 931 may include a body 932, a fixing plate 933, and a fixing recess 970. The body 932 may support the catheter 20 to prevent the catheter 20 from sagging. The fixing plate 933 may be fixed on the second partition 830. In addition, the fixing piece 914 of the first catheter cover 911 may be fitted and coupled into the fixing recess 970 as described above.

Referring to FIGS. 26B and 26C, the second catheter support part 935 may include a body 936, a fixing plate 937, a fixing recess 971, and a fitting part 938. The body 936 may support the catheter 20 to prevent the catheter 20 from sagging. The fixing plate 937 may be fixed at a mount part to be described later by the fitting part 938. According to an embodiment, the fitting part 938 may be formed in a direction different from the longitudinal direction of the catheter 20 (i.e., the transferring direction of the transfer unit 800). In addition, the fixing piece 918 of the second catheter cover 915 described above may be fitted and coupled into the fixing recess 971. The third catheter support part 939 may include a body 940, fixing plates 941 and 943, fixing recesses 972 and 973, and fitting parts 942 and 944. Functions of the components of the third catheter support part 939 may be substantially the same as those of corresponding components, and thus the descriptions thereto are omitted.

According to an embodiment, an external diameter D1 of the first catheter support part 931 may correspond to an internal diameter of the second catheter support part 935, and an external diameter D2 of the second catheter support part 935 may correspond to an internal diameter of the third catheter support part 939. Thus, the slidable telescope structure may be provided.

As a result, the first, second and third sub-catheter guide units may slide and move while folding or telescoping with respect to each other.

Hereinafter, a mount part for fixing the catheter guide unit will be described with reference to FIGS. 28 and 29.

FIG. 28 is a perspective view showing a mount part according to the second embodiment of the inventive concepts.

The mount part 950 may fix the sub-catheter guide unit through an upper portion of the mount part 950 in a state in which a lower portion of the mount part 950 is fixed on the vascular intervention robot. In detail, the mount part 950 may fix the catheter support part 930 of the sub-catheter guide unit. FIG. 28 shows a mount part fixing the third catheter support part among the mount parts, and the mount part described with reference to FIG. 28 may be used as a mount part for fixing another catheter support part.

Referring to FIG. 28, the mount part 959 may include a receiving groove 951 and a fixing pin 953.

The receiving groove 951 may provide a slit into the fitting part of the catheter support part is fitted and coupled. The slit of the receiving groove 951 may extend in a direction different from the longitudinal direction of the catheter 20 corresponding to the transferring direction of the transfer unit 800. In more detail, the slit of the receiving groove 951 may extend in a direction perpendicular to the longitudinal direction of the catheter 20. Since the slit direction of the receiving groove 951 is different from the transferring direction of the transfer unit 800, the mount part 959 may provide strong fixing force even though vibration occurs by the transferring of the transfer unit 800.

In addition, the fixing pin 953 may prevent the fitting part from escaping in a state in which the fitting part of the catheter support part is fitted in the receiving groove 951. To achieve this, the fixing pin 953 may be formed of an elastic pin that is vertically movable. As a result, the catheter guide unit may be more strongly fixed, and thus a medical doctor may stably steer the guide wire and/or the catheter through a narrow blood vessel.

As a result, the catheter guide unit may be fitted and fixed in the mount part as shown in FIG. 29. In more detail, the fitting part of the catheter support part may be fitted and fixed in the receiving groove of the mount part, and the fixing pin may fix an outer sidewall of the fitting part.

The catheter guide unit according to the second embodiment and the method of fixing the catheter guide unit are described above with reference to FIGS. 20 to 29. As a result, the sub-catheter guide units may support the catheter while folding or telescoping in states L1, L2 and L3 as shown in FIGS. 30 to 32. Hereinafter, a method of driving the vascular intervention robot according to the second embodiment of the inventive concepts will be described with reference to FIGS. 33 to 35.

Method of Driving Vascular Intervention Robot

FIGS. 33 and 35 are views showing a method of driving the vascular intervention robot according to the second embodiment of the inventive concepts. In detail, FIG. 33 shows an assembling process for preparing vascular intervention, FIG. 34 shows a process of performing the vascular intervention, and FIG. 35 shows a detaching process after the vascular intervention is finished. Hereinafter, each of the processes will be described in detail.

Referring to FIG. 33, the vascular intervention robot may be prepared to receive the catheter 20 and the guide wire 10. For example, one or some components of the vascular intervention robot may be detached to receive the catheter 20 and the guide wire 10. In detail, the catheter cover 910 of the catheter guide unit, the rotation cover 635 of the catheter rotation unit and the Y-connector 620 may be detached from the vascular intervention robot.

Meanwhile, the Y-connector 620 may receive and fix at least one of the catheter 20 and guide wire 10 at both ends of the Y-connector 620. Hereinafter, a case in which the catheter 20 is fixed at one end of the Y-connector 620 will be described for the purpose of ease and convenience in explanation. The Y-connector 620 having the catheter 20 fixed at the one end thereof may be located in the vascular intervention robot. In detail, the catheter 20 may be located on the catheter support part 930, and the Y-connector 620 may be located on the rotation body 633. Thereafter, the catheter cover 910 may be fixed on the catheter support part 930, and the rotation cover 635 may be fixed on the rotation body 633. Thus, the assembling process for the vascular intervention may be completed.

A subsequent process will be described with reference to FIG. 34. Referring to FIG. 34, the vascular intervention robot may perform translational motion and rotational motion to have at least 4 degrees of freedom. In detail, the catheter rotation unit 600 may be rotated in a direction 'A' to rotate the catheter 20. In addition, the transfer unit 800 may move in a direction 'B' to transfer the catheter rotation unit 600 and the guide wire rotation and supply unit 700.

Thus, the catheter 20 and the guide wire 10 may be transferred in the longitudinal direction. Continuously, the guide wire rotation and supply unit 700 may transfer the guide wire 10 in a direction 'C' or may rotate the guide wire 10 in a direction 'D'. Thus, the vascular intervention robot may have 4 degrees of freedom. In particular, since the catheter and the guide wire can be driven independently of each other, it is possible to provide a vascular intervention environment in which the ease of operation is enhanced or improved.

Referring to FIG. 35, one or some components may be detached after the vascular intervention is completed. In the vascular intervention robot, the component(s) disposed on the catheter 20 and the guide wire 10 may be detached, and the component(s) disposed under the catheter 20 and the guide wire 10 may also be detached. For this, the catheter cover 910 and the rotation cover 635 covering the catheter 20 and the guide wire 10 may be detached from the vascular intervention robot. Thus, the catheter 20 and the guide wire 10 may be separated from the vascular intervention robot, and the Y-connector 620 holding the catheter 20 and the guide wire 10 may also be separated from the vascular intervention robot. In addition, the catheter support part 930 and the rotation body 633 supporting lower portions of the catheter 20 and the guide wire 10 may be detached from the vascular intervention robot, and the guide wire rotation and supply unit 700 may also be detached from the vascular intervention robot. Furthermore, the guide roller part 750 and the roller driving unit 760 may be detached from the guide wire rotation and supply unit 700.

Thus, since the components being in contact with the catheter 20 and the guide wire 10 as well as the catheter 20 and the guide wire 10 are detachable from the vascular intervention robot according to the embodiment of the inventive concepts, it is possible to greatly improve the convenience of disinfection and the convenience of replacement of the component(s). In addition, since the components are attachable and detachable in up and down directions, it is possible to easily assemble and detach the components.

FIGS. 36 and 37 show images of the vascular intervention robot actually manufactured for the purpose of ease and convenience of the understanding of the vascular intervention robot according to the embodiments of the inventive concepts. In particular, the catheter cover 910, the catheter support part 930, the catheter rotation unit 600 and the guide wire rotation and supply unit 700 can be detached from the vascular intervention robot, as shown in FIG. 37. In addition, the guide roller part 750 and the roller driving unit 760 may be detached from the guide wire rotation and supply unit 700.

The vascular intervention robot according to the second embodiment of the inventive concepts is described above. Hereinafter, a vascular intervention system in which the vascular intervention robot according to the first or second embodiment is attached to a treatment bed will be described with reference to FIGS. 38 to 43.

Vascular Intervention System

FIG. 38 is a view showing a vascular intervention system according to an embodiment of the inventive concepts.

The vascular intervention system according to an embodiment of the inventive concepts may be a remote treatment system based on a master-slave apparatus. In other words, an operator (e.g., a medical doctor) may remotely control treatment at a master apparatus, and a slave apparatus may perform the treatment on a patient by the remote control. Thus, it is possible to minimize an environment in which an operator is exposed to radiation.

In detail, referring to FIG. 38, the vascular intervention system according to the embodiment of the inventive concepts may include at least one of the vascular intervention robot according to the first or second embodiment, a bed 1100, a frame 1200, and a master apparatus 1300.

The vascular intervention robot may correspond to a slave apparatus that inserts the catheter and the guide wire to a lesion region of a patient to perform the vascular intervention. The vascular intervention robot may be remotely controlled by a control signal provided from the master apparatus 1300 to be described below.

A patient 1120 may receive the treatment in a state of lying on the bed 1100. At this time, the frame 1200 may be attached to the bed 110 so as to be movable. One side of the frame 1200 may receive and fix the vascular intervention robot. For example, the vascular intervention robot may be mounted on an upper side of the frame 1200. At this time, the vascular intervention robot may be mounted to be rotated or translated with respect to the frame 1200. Another side of the frame 1200 may be attached to the bed 1100 so as to be movable. For example, the another side of the frame 1200 may be attached to a rail of the bed 1100 so as to be movable. Since the vascular intervention robot is configured to be rotated and translated with respect to the frame 1200, convenience of the treatment may be improved. This will be described later in more detail.

The master apparatus 1300 may provide an interface unit capable of remotely controlling the vascular intervention robot by an operator 1110. As a result, the operator 1110 may remotely control the vascular intervention robot, and thus it is possible to minimize radiation exposure of the operator 1110.

FIGS. 39 to 43 are views showing a frame of a vascular intervention system according to an embodiment of the inventive concepts. FIG. 39 is a partial perspective view showing the vascular intervention system according to the embodiment of the inventive concepts, and FIG. 40 is an enlarged view (in a direction 'I' of FIG. 39) showing an up-and-down direction rotation unit of the vascular intervention system according to the embodiment of the inventive concepts. FIG. 41 is an enlarged view showing a left-and-right direction movement unit of the vascular intervention system according to the embodiment of the inventive concepts, and FIG. 42 is a perspective view showing a front-and-back direction movement unit of the vascular intervention system according to the embodiment of the inventive concepts. FIG. 43 is a view showing an application example of the vascular intervention system according to the embodiment of the inventive concepts.

Referring to FIG. 39, the vascular intervention system according to an embodiment of the inventive concepts may include the vascular intervention robot, and the frame 1200 which couples the vascular intervention robot to the bed to allow the vascular intervention robot to be movable. The frame 1200 may fix the vascular intervention robot to the bed 110 in such a way that the vascular intervention robot is rotatable in up and down directions, is movable in left and right directions, and is movable in front and back directions.

Referring to FIG. 40, the frame 1200 may include an up-and-down direction rotation unit 1220. The up-and-down direction rotation unit 1220 may be, for example, a decelerator. The up-and-down direction rotation unit 1220 may be located at the center of gravity of the vascular intervention robot in the longitudinal direction of the vascular intervention robot. The up-and-down direction rotation unit 1220 may include a rotary handle 1230. An operator may operate the rotary handle 1230 to rotate the vascular intervention robot in the up and down directions (see an arrow direction of FIG. 40).

Referring to FIG. 41, the vascular intervention robot may be provided to be movable in the left and right directions. For this, the vascular intervention robot may be provided on a guide rail 1210 disposed on a top surface of the frame 1200 so as to slide in the left and right directions. At this time, a locking lever 1240 may be provided on the frame 1200. The locking lever 1240 may provide a lock in the movement of the vascular intervention robot along the guide rail 1210 in the left and right directions. Thus, an operator may operate the locking lever 1240 to move the vascular intervention robot in the left and right directions (see an arrow direction of FIG. 41).

Referring to FIG. 42, the vascular intervention robot may be provided to be movable in the front and back directions. For this, the frame 1200 may include a sliding part 1250 and a rocking lever 1260 for controlling movement of the sliding part 1250. The sliding part 1250 may have a bent shape, e.g., a "□" shape. The sliding part 1250 may receive the rail of the bed through an opened side of the "□" shape and may be coupled to the bed by the structure surrounding top and bottom ends of the rail of the bed. Thus, the sliding part 1250 may move along the rail of the bed in the front and back directions. At this time, the rocking lever 1260 may provide a lock in movement of the sliding part 1250 in the front and back directions. Thus, an operator may operate the locking lever 1260 to move the vascular intervention robot in the front and back directions (see an arrow direction of FIG. 42).

As a result, the vascular intervention robot may have 3 degrees of freedom of the rotation in the up and down directions, the movement in the left and right directions and the movement in the front and back directions with respect to the bed in the state in which the vascular intervention robot is fixed to the frame 1200.

Referring to FIG. 43(*a*), the vascular intervention robot may move in the left and right directions with respect to a patient 1120, and thus the catheter of the vascular intervention robot may face a lesion region of the patient 1120. In addition, referring to FIG. 43(*b*), the vascular intervention robot may rotate in the up and down directions and move in the front and back directions with respect to a patient 1120, and thus the catheter of the vascular intervention robot may face a lesion region of the patient 1120.

Thus, the vascular intervention system according to the inventive concepts may have 4 degrees of freedom of the vascular intervention robot according to the first or second embodiment and may additionally have 3 degrees of freedom by the frame 1200. As a result, the vascular intervention system according to the inventive concepts may have 7 degrees of freedom. Accordingly, precision of the vascular intervention and convenience of an operator may be improved.

The vascular intervention robots and the vascular intervention system according to some embodiments of the inventive concepts are described above. As described above, the components being in contact with the catheter and the guide wire may be easily attachable to and detachable from the vascular intervention robot according to some embodiments of the inventive concepts, and thus the convenience of the disinfection and the replacement of the component(s) may be improved. In addition, the vascular intervention system according to the embodiment of the inventive concepts may have 7 degrees of freedom, and the treatment convenience of an operator may be greatly improved.

The vascular intervention robot and the vascular intervention system according to some embodiments of the inventive concepts may be applied to a vascular intervention field.

According to some embodiments of the inventive concepts, the amount of the radiation exposure may be reduced, and a total size of the robot or the system may be reduced to reduce a total cost.

In addition, according to some embodiments of the inventive concepts, the total cost may further be reduced by using the existing surgical tool.

Moreover, according to some embodiments of the inventive concepts, since the covers are detached from the tubular structures, the insides of the tubular structures may be easily disinfected.

In particular, according to some embodiments of the inventive concepts, the components being in contact with the catheter and the guide wire may be detachable and attachable, and thus the convenience of the disinfection and the replacement of the component(s) may be improved.

According to some embodiments of the inventive concepts, the degree of freedom of the vascular intervention robot may be improved, and thus the convenience of the treatment may also be improved.

While the inventive concepts have been described with reference to exemplary embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. A vascular intervention robot comprising:
a catheter rotation unit for rotating a catheter on an axis parallel to a longitudinal direction of the catheter;
a guide wire rotation and supply unit that is provided at one side of the catheter rotation unit and that is provided for transferring a guide wire in a longitudinal direction of the guide wire and for rotating the guide wire on an axis parallel to the longitudinal direction of the guide wire in a state in which the guide wire is inserted in the catheter;
a transfer unit for transferring the catheter rotation unit and the guide wire rotation and supply unit in the longitudinal direction of the catheter; and
an expanding and contracting unit that is provided at another side of the catheter rotation unit and that is expandable and contractible along the longitudinal direction of the catheter while supporting the catheter when the transfer unit transfers the catheter rotation unit and the guide wire rotation and supply unit in the longitudinal direction of the catheter,
a support part comprising: a base part having a flat plate shape; a first partition provided at one end of the base part; a second partition provided at another end of the base part; and a support bar extending from the first partition to the second partition,
wherein the expanding and contracting unit comprises: a plurality of tubular structures continuously provided from the other side of the catheter rotation unit to support the catheter; and a plurality of supporters respectively supporting the plurality of tubular structures, wherein an end of the tubular structure farthest from the other end of the catheter rotation unit is fixed at the second partition, wherein a second insertion hole in which the support bar is inserted is provided in at least one supporter of the plurality of supporters, and the at least one supporter having the second insertion hole moves along the support bar when the transfer unit moves on the base part, and wherein the catheter rotation unit, the guide wire rotation and supply unit and the expanding and contracting unit, which are in contact with at least one of the catheter and the guide wire, are detachable from the vascular intervention robot.

2. The vascular intervention robot of claim 1, wherein Y-connector is coupled to the catheter rotation unit, wherein the Y-connector comprises:

a body having a pipe shape, wherein the catheter is fixed at one end of the body; and the guide wire is inserted into the body from another end of the body and is inserted into the catheter at the one end of the body; and a branch portion having a pipe shape and coupled to the body between the one end and the other end of the body so as to be connected to an inside of the body, wherein a fluid is injected into the branch portion.

3. The vascular intervention robot of claim 2, wherein the catheter rotation unit comprises: a pad being in contact with top and bottom portions of the Y-connector to fix the Y-connector.

4. The vascular intervention robot of claim 1, wherein the guide wire rotation and supply unit comprises:

a guide wire supply unit comprising: two rollers facing each other; and a roller driving unit driving at least one of the two rollers, wherein the guide wire is inserted between the two rollers and is transferred in the longitudinal direction of the guide wire when the two rollers are driven by the roller driving unit.

5. The vascular intervention robot of claim 4, wherein the guide wire rotation and supply unit further comprises:

a guide wire rotation unit comprising: a guide wire rotor supporting the rollers and the roller driving unit; and a guide wire driver rotating the guide wire rotor on the axis parallel to the longitudinal direction of the guide wire.

6. The vascular intervention robot of claim 1, wherein the catheter rotation unit and the guide wire rotation and supply unit are disposed on the transfer unit, wherein the transfer unit moves in the longitudinal direction of the catheter on the base part by rack and pinion, wherein a first insertion hole in which the support bar is inserted is provided in the transfer unit, and wherein the transfer unit moves along the support bar when the transfer unit moves on the base part.

7. The vascular intervention robot of claim 1, wherein an Nth tubular structure from the side of the catheter rotation unit slides inside and outside an N−1th tubular structure or N+1th tubular structure from the side of the catheter rotation unit, such that the expanding and contracting unit is expandable and contractible in the longitudinal direction of the catheter.

8. The vascular intervention robot of claim 7, wherein each of the tubular structures comprises:

a support structure supporting the catheter; and a cover which is coupled to an upper side of the support structure and is detachable.

9. A vascular intervention system comprising:

the vascular intervention robot of claim 1; and a frame fixing the vascular intervention robot in such a way that the vascular intervention robot is movable relatively with respect to a treatment bed, wherein the frame comprises: an up-and-down direction rotation unit adjusting an angle of the vascular intervention robot in up and down directions.

* * * * *